(12) United States Patent
Glossop

(10) Patent No.: US 10,582,879 B2
(45) Date of Patent: Mar. 10, 2020

(54) METHOD AND APPARATUS FOR REGISTRATION, VERIFICATION AND REFERENCING OF INTERNAL ORGANS

(71) Applicant: KONINKLIJKE PHILIPS N.V., Eindhoven (NL)

(72) Inventor: Neil David Glossop, Toronto (CA)

(73) Assignee: PHILIPS ELECTRONICS LTD, Markham, ON (CA)

( * ) Notice: Subject to any disclaimer, the term of this patent is extended or adjusted under 35 U.S.C. 154(b) by 30 days.

(21) Appl. No.: 15/281,137

(22) Filed: Sep. 30, 2016

(65) Prior Publication Data
US 2017/0079554 A1 Mar. 23, 2017

Related U.S. Application Data

(63) Continuation of application No. 11/059,336, filed on Feb. 17, 2005, now abandoned.
(Continued)

(51) Int. Cl.
*A61B 8/00* (2006.01)
*A61B 5/06* (2006.01)
(Continued)

(52) U.S. Cl.
CPC .............. *A61B 5/066* (2013.01); *A61B 5/02* (2013.01); *A61B 5/031* (2013.01); *A61B 5/061* (2013.01);
(Continued)

(58) Field of Classification Search
CPC ................................ A61B 5/0422; A61B 5/06
See application file for complete search history.

(56) References Cited

U.S. PATENT DOCUMENTS

| 3,021,842 | A | 2/1962 | Flood |
| 4,080,706 | A | 3/1978 | Heilman et al. ................. 29/173 |

(Continued)

FOREIGN PATENT DOCUMENTS

| AU | 6367896 | 2/1997 |
| AU | 722539 | 8/2000 |

(Continued)

OTHER PUBLICATIONS

TRA029—RITA StarBurst Soft Tissue Access System and RITA StarBurst Hard Tissue Access System, http://www.ritamedical.com, Rita Medical Systems, Inc., copyright 2002, , 8 pages.
(Continued)

*Primary Examiner* — Joseph M Santos Rodriguez

(57) ABSTRACT

Systems and methods for registering, verifying, dynamically referencing, and navigating an anatomical region of interest of a patient are provided. In one embodiment, the anatomical region of interest is imaged using an imaging device such as, for example, an x-ray device. A tracked registration device may then be removably inserted following a path within the anatomical region and the position of the registration device may be sampled by a tracking device as the registration device is moved within the anatomical region through the catheter. The sampled position data is registered to the image data to register the path to the anatomical region of interest. The same or a similar device may be used to dynamically reference the movements affecting the anatomical region and modify the registration in real time. The registration may also be verified.

32 Claims, 11 Drawing Sheets

Related U.S. Application Data

(60) Provisional application No. 60/544,344, filed on Feb. 17, 2004, provisional application No. 60/605,139, filed on Aug. 30, 2004, provisional application No. 60/626,422, filed on Nov. 10, 2004, provisional application No. 60/626,488, filed on Nov. 10, 2004.

(51) Int. Cl.

| | | |
|---|---|---|
| *A61B 5/00* | (2006.01) | |
| *A61B 6/00* | (2006.01) | |
| *A61B 8/08* | (2006.01) | |
| *A61B 34/20* | (2016.01) | |
| *A61B 5/02* | (2006.01) | |
| *A61B 5/03* | (2006.01) | |
| *A61B 5/08* | (2006.01) | |
| *A61B 5/12* | (2006.01) | |
| *A61B 5/20* | (2006.01) | |
| *A61B 6/03* | (2006.01) | |
| *A61B 8/12* | (2006.01) | |
| *A61M 25/01* | (2006.01) | |
| *A61B 90/00* | (2016.01) | |
| *A61B 6/12* | (2006.01) | |
| *A61B 5/042* | (2006.01) | |
| *A61B 34/10* | (2016.01) | |

(52) U.S. Cl.
CPC ............ *A61B 5/062* (2013.01); *A61B 5/08* (2013.01); *A61B 5/12* (2013.01); *A61B 5/20* (2013.01); *A61B 5/418* (2013.01); *A61B 5/42* (2013.01); *A61B 5/43* (2013.01); *A61B 5/7221* (2013.01); *A61B 6/032* (2013.01); *A61B 6/037* (2013.01); *A61B 6/5247* (2013.01); *A61B 8/0841* (2013.01); *A61B 8/12* (2013.01); *A61B 8/4245* (2013.01); *A61B 8/481* (2013.01); *A61B 8/5238* (2013.01); *A61B 8/5261* (2013.01); *A61B 34/20* (2016.02); *A61M 25/0108* (2013.01); *A61M 25/0127* (2013.01); *A61B 5/03* (2013.01); *A61B 5/042* (2013.01); *A61B 5/7285* (2013.01); *A61B 6/12* (2013.01); *A61B 6/541* (2013.01); *A61B 8/0833* (2013.01); *A61B 8/4263* (2013.01); *A61B 2034/107* (2016.02); *A61B 2034/2051* (2016.02); *A61B 2034/2055* (2016.02); *A61B 2034/2061* (2016.02); *A61B 2090/364* (2016.02); *A61B 2090/374* (2016.02); *A61B 2090/376* (2016.02); *A61B 2090/3925* (2016.02); *A61B 2090/3954* (2016.02); *A61B 2090/3966* (2016.02); *A61B 2562/222* (2013.01); *A61M 25/0105* (2013.01)

(56) References Cited

U.S. PATENT DOCUMENTS

| | | | |
|---|---|---|---|
| 4,279,252 A | 7/1981 | Martin | 128/349 R |
| 4,697,595 A | 10/1987 | Breyer et al. | 128/660 |
| 4,722,056 A | 1/1988 | Roberts et al. | 364/413 |
| 4,777,951 A | 10/1988 | Cribier et al. | 128/344 |
| 4,887,606 A | 12/1989 | Yock et al. | 128/662.05 |
| 4,895,168 A | 1/1990 | Machek | 128/772 |
| 4,935,019 A | 6/1990 | Papp, Jr. | 604/362 |
| 4,961,433 A | 10/1990 | Christian | 128/772 |
| 5,014,708 A | 5/1991 | Hayashi et al. | 128/653 R |
| 5,042,486 A | 8/1991 | Pfeiler et al. | 128/653 R |
| 5,045,080 A | 9/1991 | Dyer et al. | 604/362 |
| 5,085,659 A | 2/1992 | Rydell | 606/47 |
| 5,116,345 A | 5/1992 | Jewell et al. | 606/130 |
| 5,187,658 A | 2/1993 | Cline et al. | 364/413.13 |
| 5,204,625 A | 4/1993 | Cline et al. | 324/306 |
| 5,207,675 A | 5/1993 | Canady | 606/40 |
| 5,211,165 A | 5/1993 | Dumoulin et al. | 128/653.1 |
| 5,221,283 A | 6/1993 | Chang | 606/130 |
| 5,247,935 A | 9/1993 | Cline et al. | 128/653.2 |
| 5,251,127 A | 10/1993 | Raab | 364/413.13 |
| 5,251,635 A | 10/1993 | Dumoulin et al. | 128/653.2 |
| 5,255,680 A | 10/1993 | Darrow et al. | 128/653.1 |
| 5,265,610 A | 11/1993 | Darrow et al. | 128/653.1 |
| 5,271,400 A | 12/1993 | Dumoulin et al. | 128/653.2 |
| 5,275,165 A | 1/1994 | Ettinger et al. | 128/653.2 |
| 5,290,266 A | 3/1994 | Rohling et al. | 604/272 |
| 5,291,010 A | 3/1994 | Tsuji | 250/208.1 |
| 5,291,890 A | 3/1994 | Cline et al. | 128/653.2 |
| 5,304,933 A | 4/1994 | Vavrek et al. | 324/318 |
| 5,305,203 A | 4/1994 | Raab | 364/413.13 |
| 5,307,812 A | 5/1994 | Hardy et al. | 128/653.2 |
| 5,318,025 A | 6/1994 | Dumoulin et al. | 128/653.2 |
| 5,323,779 A | 6/1994 | Hardy et al. | 128/653.2 |
| 5,327,884 A | 7/1994 | Hardy et al. | 128/653.2 |
| 5,353,808 A | 10/1994 | Viera | 128/772 |
| 5,365,927 A | 11/1994 | Roemer et al. | 128/653.2 |
| 5,368,031 A | 11/1994 | Cline et al. | 128/653.2 |
| 5,368,032 A | 11/1994 | Cline et al. | 128/653.2 |
| 5,377,678 A | 1/1995 | Dumoulin et al. | 128/653.1 |
| 5,383,454 A | 1/1995 | Bucholz | 128/653.1 |
| 5,383,465 A | 1/1995 | Lesny et al. | 128/662.05 |
| 5,386,828 A | 2/1995 | Owens et al. | 128/653.1 |
| 5,389,101 A | 2/1995 | Heilbrun et al. | 606/130 |
| 5,391,199 A | 2/1995 | Ben-Haim | 607/122 |
| 5,396,905 A | 3/1995 | Newman et al. | 128/849 |
| 5,400,383 A | 3/1995 | Yassa et al. | 378/98.2 |
| 5,409,444 A * | 4/1995 | Kensey | A61B 17/12109 600/16 |
| 5,437,277 A | 8/1995 | Dumoulin et al. | 128/653.1 |
| 5,443,066 A | 8/1995 | Dumoulin et al. | 128/653.1 |
| 5,443,068 A | 8/1995 | Cline et al. | 128/653.5 |
| 5,445,150 A | 8/1995 | Dumoulin et al. | 128/653.1 |
| 5,465,732 A | 11/1995 | Abele | 128/772 |
| 5,480,382 A | 1/1996 | Hammerslag et al. | 604/95 |
| 5,490,840 A | 2/1996 | Uzgiris et al. | 604/22 |
| 5,493,598 A | 2/1996 | Yassa et al. | 378/98.2 |
| 5,526,812 A | 6/1996 | Dumoulin et al. | 128/653.1 |
| 5,526,814 A | 6/1996 | Cline et al. | 128/653.2 |
| 5,558,091 A | 9/1996 | Acker et al. | 128/653.1 |
| 5,603,318 A | 2/1997 | Heilbrun et al. | 128/630 |
| 5,638,819 A | 6/1997 | Manwaring et al. | 600/424 |
| 5,645,065 A | 7/1997 | Shapiro et al. | 128/653.1 |
| 5,646,524 A | 7/1997 | Gilboa | 324/207.17 |
| 5,646,525 A | 7/1997 | Gilboa | 324/207.17 |
| 5,647,373 A | 7/1997 | Paltieli | 128/749 |
| 5,705,014 A | 1/1998 | Schenck et al. | 156/272.4 |
| 5,713,858 A | 2/1998 | Heruth et al. | 604/93 |
| 5,715,166 A | 2/1998 | Besl et al. | 364/474.24 |
| 5,715,822 A | 2/1998 | Watkins et al. | 128/653.5 |
| 5,740,802 A | 4/1998 | Nafis et al. | 128/653.1 |
| 5,749,835 A | 5/1998 | Glantz | 600/424 |
| 5,769,790 A | 6/1998 | Watkins et al. | 600/439 |
| 5,769,861 A | 6/1998 | Vilsmeier | 606/130 |
| 5,848,969 A | 12/1998 | Panescu et al. | 600/462 |
| 5,857,032 A | 1/1999 | Wang et al. | 382/154 |
| 5,868,673 A | 2/1999 | Vesely | 600/407 |
| 5,873,845 A | 2/1999 | Cline et al. | 601/3 |
| 5,880,976 A | 3/1999 | DiGioia III et al. | 364/578 |
| 5,931,786 A | 8/1999 | Whitmore, III et al. | 600/459 |
| 5,944,023 A | 8/1999 | Johnson et al. | 128/899 |
| 5,978,696 A | 11/1999 | VomLehn et al. | 600/411 |
| 6,016,439 A | 1/2000 | Acker | 600/411 |
| 6,036,682 A | 3/2000 | Lange et al. | 604/529 |
| 6,073,043 A | 6/2000 | Schneider | 600/424 |
| 6,097,978 A | 8/2000 | Demarais et al. | 600/429 |
| 6,106,476 A | 8/2000 | Corl et al. | 600/486 |
| 6,141,576 A | 10/2000 | Littmann et al. | 600/381 |
| 6,147,480 A | 11/2000 | Osadchy et al. | 324/67 |
| 6,165,184 A | 12/2000 | Verdura et al. | 606/148 |
| 6,188,355 B1 | 2/2001 | Gilboa | 342/448 |
| 6,196,980 B1 | 3/2001 | Akerfeldt et al. | 600/585 |
| 6,203,493 B1 | 3/2001 | Ben-Haim | 600/117 |
| 6,203,543 B1 | 3/2001 | Glossop | 606/60 |
| 6,205,411 B1 | 3/2001 | DiGioia, III et al. | 703/11 |

(56) References Cited

U.S. PATENT DOCUMENTS

| | | | |
|---|---|---|---|
| 6,210,339 B1 | 4/2001 | Kiepen et al. | 600/486 |
| 6,216,029 B1 | 4/2001 | Paltieli | 600/427 |
| 6,226,543 B1 | 5/2001 | Gilboa et al. | 600/407 |
| 6,233,476 B1 | 5/2001 | Strommer et al. | 600/424 |
| 6,235,038 B1 | 5/2001 | Hunter et al. | 606/130 |
| 6,241,690 B1 | 6/2001 | Burkett et al. | 600/585 |
| 6,266,551 B1 | 7/2001 | Osadchy et al. | 600/424 |
| 6,266,552 B1 | 7/2001 | Slettenmark | 600/424 |
| 6,272,370 B1 | 8/2001 | Gillies et al. | 600/411 |
| 6,272,371 B1 | 8/2001 | Shlomo | 600/424 |
| 6,285,898 B1 | 9/2001 | Ben-Haim | 600/374 |
| 6,285,903 B1 | 9/2001 | Rosenthal et al. | 600/433 |
| 6,288,785 B1 | 9/2001 | Frantz et al. | 356/614 |
| 6,308,089 B1 | 10/2001 | von der Ruhr et al. | 600/338 |
| 6,314,310 B1 | 11/2001 | Ben-Haim et al. | 600/424 |
| 6,317,621 B1 | 11/2001 | Graumann et al. | 600/424 |
| 6,332,089 B1 | 12/2001 | Acker et al. | 600/424 |
| 6,336,906 B1 | 1/2002 | Hammarstrom et al. | 600/585 |
| 6,338,716 B1 | 1/2002 | Hossack et al. | 600/459 |
| 6,356,783 B1 | 3/2002 | Hubbard, Jr. | 600/546 |
| 6,380,732 B1 | 4/2002 | Gilboa | 324/207.17 |
| 6,381,485 B1 | 4/2002 | Hunter et al. | 600/407 |
| 6,383,174 B1 | 5/2002 | Eder | 606/1 |
| 6,385,482 B1 | 5/2002 | Boksberger et al. | 600/424 |
| 6,427,079 B1 | 7/2002 | Schneider et al. | 600/424 |
| 6,442,417 B1 | 8/2002 | Shahidi et al. | 600/429 |
| 6,468,265 B1 | 10/2002 | Evans et al. | 606/1 |
| 6,473,635 B1 | 10/2002 | Rasche | 600/428 |
| 6,484,118 B1 | 11/2002 | Govari | 702/150 |
| 6,493,589 B1 | 12/2002 | Medhkour et al. | 607/99 |
| 6,498,944 B1 | 12/2002 | Ben-Haim et al. | 600/424 |
| 6,499,488 B1 | 12/2002 | Hunter et al. | 128/899 |
| 6,500,114 B1 | 12/2002 | Petitto et al. | 600/156 |
| 6,512,958 B1 | 1/2003 | Swoyer et al. | 607/117 |
| 6,529,758 B2 | 3/2003 | Shahidi | 600/407 |
| 6,547,782 B1 | 4/2003 | Taylor | 606/14 |
| 6,558,333 B2 | 5/2003 | Gilboa et al. | 600/466 |
| 6,574,492 B1 | 6/2003 | Ben-Haim et al. | 600/374 |
| 6,574,498 B1 | 6/2003 | Gilboa | 600/424 |
| 6,580,938 B1 | 6/2003 | Acker | 600/424 |
| 6,585,654 B2 | 7/2003 | White et al. | 600/463 |
| 6,588,333 B1 | 7/2003 | Homer et al. | 101/32 |
| 6,591,129 B1 | 7/2003 | Ben-Haim et al. | 600/424 |
| 6,593,127 B1 | 7/2003 | McKinnon | 600/411 |
| 6,593,884 B1 | 7/2003 | Gilboa et al. | 342/448 |
| 6,615,155 B2 | 9/2003 | Gilboa | 702/150 |
| 6,619,838 B2 | 9/2003 | Bencini et al. | 378/190 |
| 6,628,987 B1 | 9/2003 | Hill et al. | 607/9 |
| 6,671,538 B1 | 12/2003 | Ehnholm et al. | 600/425 |
| 6,690,963 B2 | 2/2004 | Ben-Haim et al. | 600/424 |
| 6,702,780 B1 | 3/2004 | Gilboa et al. | 604/95.04 |
| 6,711,429 B1 | 3/2004 | Gilboa et al. | 600/407 |
| 6,719,700 B1 | 4/2004 | Willis | 600/462 |
| 6,735,471 B2 | 5/2004 | Hill et al. | 607/2 |
| 6,748,112 B1 | 6/2004 | Nguyen et al. | 382/203 |
| 6,753,873 B2 | 6/2004 | Dixon et al. | 345/542 |
| 6,754,376 B1 | 6/2004 | Turek et al. | 382/131 |
| 6,782,287 B2 | 8/2004 | Grzeszczuk et al. | 600/424 |
| 6,783,536 B2 | 8/2004 | Vilsmeier et al. | 606/130 |
| 6,785,571 B2 | 8/2004 | Glossop | 600/424 |
| 6,788,967 B2 | 9/2004 | Ben-Haim et al. | 600/424 |
| 6,792,303 B2 | 9/2004 | Taimisto | 600/424 |
| 6,893,429 B2 | 5/2005 | Petersen | 604/537 |
| 6,895,268 B1 | 5/2005 | Rahn et al. | 600/429 |
| 6,916,290 B2 | 7/2005 | Hedengren et al. | 600/549 |
| 7,085,400 B1 | 8/2006 | Holsing et al. | 382/103 |
| 7,386,339 B2 | 6/2008 | Strommer et al. | 600/424 |
| 7,570,791 B2 | 8/2009 | Frank et al. | 382/132 |
| 2001/0008972 A1 | 7/2001 | Gielen | 607/45 |
| 2001/0011175 A1 | 8/2001 | Hunter et al. | 606/130 |
| 2001/0031919 A1 | 10/2001 | Strommer et al. | 600/424 |
| 2001/0031985 A1 | 10/2001 | Gilboa et al. | 607/1 |
| 2001/0036245 A1 | 11/2001 | Kienzle, III et al. | 378/4 |
| 2001/0038354 A1 | 11/2001 | Gilboa | 342/450 |
| 2001/0039419 A1 | 11/2001 | Francischelli et al. | 606/42 |
| 2001/0047133 A1 | 11/2001 | Gilboa et al. | 600/429 |
| 2002/0005719 A1 | 1/2002 | Gilboa et al. | 324/309 |
| 2002/0038102 A1 | 3/2002 | McFarlin et al. | 604/30 |
| 2002/0042571 A1 | 4/2002 | Gilboa et al. | 600/429 |
| 2002/0049375 A1 | 4/2002 | Strommer et al. | 600/407 |
| 2002/0049451 A1 | 4/2002 | Parmer et al. | 606/108 |
| 2002/0062203 A1 | 5/2002 | Gilboa | 702/150 |
| 2002/0074005 A1 | 6/2002 | Hogg et al. | 128/899 |
| 2002/0087101 A1 | 7/2002 | Barrick et al. | 600/587 |
| 2002/0143317 A1 | 10/2002 | Glossop | 604/529 |
| 2002/0156363 A1 | 10/2002 | Hunter et al. | 600/410 |
| 2002/0156417 A1 | 10/2002 | Rich et al. | 604/65 |
| 2002/0165448 A1 | 11/2002 | Ben-Haim et al. | 600/424 |
| 2002/0165468 A1 | 11/2002 | Tolkowsky et al. | 600/587 |
| 2003/0018251 A1 | 1/2003 | Solomon | 600/427 |
| 2003/0021455 A1 | 1/2003 | Dixon et al. | 382/132 |
| 2003/0028233 A1 | 2/2003 | Vardi et al. | 623/1.11 |
| 2003/0030004 A1 | 2/2003 | Dixon et al. | 250/370.09 |
| 2003/0074011 A1 | 4/2003 | Gilboa et al. | 606/130 |
| 2003/0092988 A1 | 5/2003 | Makin | 600/439 |
| 2003/0114778 A1 | 6/2003 | Vilsmeier et al. | 600/585 |
| 2003/0114846 A1 | 6/2003 | Fuimaono et al. | 606/41 |
| 2003/0130576 A1 | 7/2003 | Seeley et al. | 600/426 |
| 2003/0171680 A1 | 9/2003 | Paltieli | 600/459 |
| 2003/0171739 A1 | 9/2003 | Murphy et al. | 606/1 |
| 2003/0208102 A1 | 11/2003 | Gilboa | 600/41 |
| 2003/0208296 A1 | 11/2003 | Brisson et al. | 700/117 |
| 2003/0216639 A1 | 11/2003 | Gilboa et al. | 600/424 |
| 2003/0220557 A1 | 11/2003 | Cleary et al. | 600/409 |
| 2004/0019274 A1 | 1/2004 | Galloway, Jr. et al. | 600/425 |
| 2004/0024309 A1 | 2/2004 | Ferre et al. | 600/424 |
| 2004/0034297 A1 | 2/2004 | Darrow et al. | 600/407 |
| 2004/0034300 A1 | 2/2004 | Verard et al. | 600/424 |
| 2004/0036867 A1 | 2/2004 | Jedamzik | 356/243.1 |
| 2004/0077942 A1 | 4/2004 | Hall et al. | 600/428 |
| 2004/0078036 A1 | 4/2004 | Keidar | 606/41 |
| 2004/0097804 A1 | 5/2004 | Sobe | 600/424 |
| 2004/0097805 A1 | 5/2004 | Verard et al. | 600/428 |
| 2004/0097806 A1 | 5/2004 | Hunter et al. | 600/434 |
| 2004/0138548 A1 | 7/2004 | Strommer et al. | 600/407 |
| 2004/0143188 A1 | 7/2004 | Barzell et al. | 600/439 |
| 2004/0147837 A1 | 7/2004 | Macaulay et al. | 600/424 |
| 2004/0147939 A1 | 7/2004 | Rabkin et al. | 606/108 |
| 2004/0158146 A1 | 8/2004 | Mate et al. | 600/427 |
| 2004/0221853 A1 | 11/2004 | Miller | 128/207.14 |
| 2004/0234933 A1 | 11/2004 | Dawson et al. | 434/262 |
| 2004/0249267 A1 | 12/2004 | Gilboa | 600/424 |
| 2004/0254458 A1 | 12/2004 | Govari | 600/437 |
| 2005/0033149 A1 | 2/2005 | Strommer et al. | 600/407 |
| 2005/0038337 A1 | 2/2005 | Edwards | 600/424 |
| 2005/0049520 A1 | 3/2005 | Nakao | 600/562 |
| 2005/0054900 A1 | 3/2005 | Mawn et al. | 600/156 |
| 2005/0059886 A1 | 3/2005 | Webber | 600/426 |
| 2005/0085715 A1 | 4/2005 | Dukesherer et al. | 600/424 |
| 2005/0085720 A1 | 4/2005 | Jascob et al. | 600/424 |
| 2005/0085793 A1 | 4/2005 | Glossop | 604/529 |
| 2005/0107688 A1 | 5/2005 | Strommer | 600/424 |
| 2005/0182295 A1 | 8/2005 | Soper et al. | 600/117 |
| 2005/0182319 A1 | 8/2005 | Glossop | 600/424 |
| 2005/0228270 A1 | 10/2005 | Lloyd et al. | 600/424 |
| 2006/0147100 A1 | 7/2006 | Fitzpatrick | 382/131 |
| 2007/0032862 A1 | 2/2007 | Weber et al. | 623/1.34 |

FOREIGN PATENT DOCUMENTS

| | | |
|---|---|---|
| BR | 9609484 | 12/1999 |
| CA | 2226938 | 2/1997 |
| DE | 69420228 D | 9/1999 |
| DE | 69420228 T | 4/2000 |
| DE | 19845267 | 5/2000 |
| EP | 0 845 959 | 6/1998 |
| EP | 0 654 244 | 8/1999 |
| EP | 1466552 | 10/2004 |
| IL | 0107523 | 1/2000 |
| IL | 0114610 | 7/2000 |
| JP | 10-277047 | 10/1998 |
| JP | 2000500031 T | 1/2000 |
| JP | 2005152463 | 6/2005 |

(56) References Cited

FOREIGN PATENT DOCUMENTS

| WO | WO 97/03609 | 2/1997 |
|---|---|---|
| WO | WO 98/56295 | 12/1998 |
| WO | WO 00/22904 | 4/2000 |

OTHER PUBLICATIONS

TRA030—Cool-tip RF Tissue Ablation System, Cool-tip RF System, and Cool-tip Electrodes, http://www.valleylab.com/static/cooltip/products.html, Valleylab, copyright 2004, 4 pages.
TRA031—LeVeen Needle Electrode, Boston Scientific, printed from http://www.bostonscientific.com/med_specialty/deviceDetail.jhtml?task=_tskBasicDevice . . . , printed on Sep. 13, 2004, 1 page.
TRA032—Bradford J. Wood et al., "Navigation with Electromagnetic Tracking for Interventional Radiology Procedures: A Feasibility Study", Laboratory Investigations, *Journal of Vasc. Interv. Radiol.*, vol. 16, 2005, pp. 493-505.
TRA024—Knaan, Dotan, et al., Effective Intensity-Based 2D/3D Rigid Registration Between Fluoroscopic X-Ray and CT, *MICCAI*, vol. 1, 2003, pp. 351-358.
TRA025—Gee, A. H., et al., "3D Ultrasound Probe Calibration Without a Position Sensor", CUED/F-INFENG/TR 488, University of Cambridge, Department of Engineering, Sep. 2004, 21 pages.
TRA026—Lindseth, Frank, et al., "Probe Calibration for Freehand 3D Ultrasound Reconstruction and Surgical Navigation", Dec. 2002, 27 pages.
TRA027—Fuchs, Henry, et al., "Towards Performing Ultrasound-Guided Needle Biopsies from Within a Head-Mounted Display", University of North Carolina, Department of Computer Science, 1996, 10 pages; [Lecture Notes in Computer Science; vol. 1131 archive Proceedings of the 4th International Conference on Visualization in Biomedical Computing table of contents, pp. 591-600 Year of Publication: 1996, ISBN:3-540-61649-7; Hamburg, Germany, Sep 22-25, 1996).].
TRA028—Henry Fuchs, Andrei State, Mark A. Livingston, William F. Garrett, Gentaro Hirota, Mary Whitton and Etta D. Pisano (MD). "Virtual Environments Technology to Aid Needle Biopsies of the Breast: An Example of Real-Time Data Fusion." Proceedings of Medicine Meets Virtual Reality:4 (Jan. 17-20, 1996, San Diego, California), IOS Press, Amsterdam, Jan 1996.
TRA001—Tanase, Dafina, et al., "Magnetic Sensors for Use on Guide Wires or Catheters", in *SeSens* 2001, in press 2002, pp. 868-872.
TRA002—Solomon, Stephen B., et al., "Three-Dimensional CT-Guided Bronchoscopy with a Real-Time Electromagnetic Position Sensor: A Comparison of Two Image Registration Methods", *Chest*, vol. 118, No. 6, Dec. 2000, pp. 1783-1787.
TRA003—Solomon, Stephen B., et al., "Real-Time Cardiac Catheter Navigation on Three-Dimensional CT Images", *Journal of Interventional Cardiac Electrophysiology*, vol. 8, 2003, pp. 27-36.
TRA004—Palti-Wasserman, Daphna, etal., "Identifying and Tracking a Guide Wire in the Coronary Arteries During Angioplasty from X-Ray Images", *IEEE Transactions on Biomedical Engineering*, vol. 44, No. 2, Feb. 1997, pp. 152-164.
TRA005—Baert, Shirley A. M., et al., "Endpoint Localization in Guide Wire Tracking During Endovascular Interventions", *Academic Radiology*, vol. 10, No. 12, Dec. 2003, pp. 1424-1432.
TRA006—Baert, Shirley A. M., et al., "Three-Dimensional Guide-Wire Reconstruction from Biplane Image Sequences for Integrated Display in 3-D Vasculature", *IEEE Transactions on Medical Imaging*, vol. 22, No. 10, Oct. 2003, pp. 1252-1258.

TRA007—Baert, Shirley A. M., et al., "Guide-Wire Tracking During Endovascular Interventions", *IEEE Transactions on Medical Imaging*, vol. 22, No. 8, Aug. 2003, pp. 965-972.
TRA008—Kobashi, Keiji, et al., "A New Biomechanical Model Based Approach on Brain Shift Compensation", *MICCAI 2003*, LNCS 2878, 2003, pp. 59-66.
TRA009—Timinger, Holger, et al., "Motion Compensation for Interventional Navigation on 3D Static Roadmaps Based on an Affine Model and Gating", *Physics in Medicine and Biology*, vol. 49, 2004, pp. 719-732.
TRA010—Lorigo, Liana M., et al., "Curves: Curve Evolution for Vessel Segmentation", *Medical Image Analysis*, vol. 5, 2001, pp. 195-206 (pp. 1-14).
TRA011—Chassat, Fabrice, et al., "Experimental Protocol of Accuracy Evaluation of 6-D Localizers for Computer-Integrated Surgery: Application to Four Optical Localizers", *MICCAI 98*, vol. 1496, Oct. 1998, Cambridge, Massachusetts U.S.A., p. 277-284.
TRA012—Tsai, Roger Y., "A Versatile Camera Calibration Technique for High-Accuracy 3D Machine Vision Metrology Using Off-the-Shelf TV Cameras and Lenses", *IEEE Journal of Robotics and Automation*, vol. RA-3, No. 4, Aug. 1987, pp. 323-344.
TRA013—"Semi-Automatic Registration for Image Guided Surgery", Traxtal poster presented at CAOS '99 (Computer Assisted Orthopaedic Surgery, 4th International Symposium), MICCAI, Mar. 17-19, 1999, Davos, Switzerland, 1 page.
TRA014—Wu, Xiaohui, etal., "A Direction Space Interpolation Technique for Calibration of Electromagnetic Surgical Navigation Systems", Lecture Notes in Computer Science Medical Image Computing and Computer-Assisted Intervention, *MICCAI 2003*, LNCS 2879, Publisher: Springer-Verlag Heidelberg, 2003, pp. 215-222.
TRA015—Livyatan, Harel, "Calibration and Gradient-Based Rigid Registration of Fluoroscopic X-raysto CT, for Intra Operative Navigation", Master of Science Thesis, supervised by Prof. Leo Joskowicz, School of Computer Science and Engineering, The Hebrew University of Jerusalem, Israel, Jul. 27, 2003, 92 pages.
TRA016—SuperDimension, Ltd, web page, updated in Sep. 2005, 1 page.
TRA017—Schweikard, Achim, et al., "Robotic Motion Compensation for Respiratory Movement During Radiosurgery", *Computer Aided Surgery*, vol. 5, 2000, pp. 263-277.
TRA018—Solomon, Stephen B., et al., "Real-Time Bronchoscope Tip Localization Enables Three-Dimensional CT Image Guidance for Transbronchial Needle Aspiration in Swine", *Chest*, Volume 114, No. 5, Nov. 1998, pp. 1405-1410.
TRA019—Ellsmere, James, et al., "A Navigation System for Augmenting Laparoscopic Ultrasound", Center for Integration of Medicine and Innovative Technology, Cambridge, Massachusetts, 8 pages.
TRA020—Hofstetter, R., et al., "Fluoroscopy Based Surgical Navigation—Concept and Clinical Applications", Maurice E. Muller Institute for Biomechanics, University of Bern, Switzerland, 1997, 3 pages.
TRA021—Tapper, Michael, et al., "Problems Encountered in the Implementation of Tsai's Algorithm for Camera Calibration", *Proc. 2002 Australasian Conference on Robotics and Automation*, Auckland, Nov. 27-29, 2002, pp. 66-70.
TRA022—Summers, Ronald M., et al., "Colonic Polyps: Complementary Role of Computer-Aided Detection in CT Colonography", *Radiology*, vol. 225, No. 2, Nov. 2002, pp. 391-399.
TRA023—Hara, A. K., et al., "Reducing Data Size and Radiation Dose for CT Colonography", *AJR*, vol. 168, May 1997, pp. 1181-1184.

* cited by examiner

METHOD AND APPARATUS FOR REGISTRATION, VERIFICATION AND REFERENCING OF INTERNAL ORGANS

RELATED APPLICATIONS

This is a continuation of prior application Ser. No. 11/059,336 filed Feb. 17, 2005. This application claims priority to U.S. Provisional Patent Application Ser. No. 60/544,344, filed Feb. 17, 2004; U.S. Provisional Patent Application Ser. No. 60/605,139 filed Aug. 30, 2004; U.S. Provisional Patent Application Ser. No. 60/626,422, filed Nov. 10, 2004; and to U.S. Provisional Patent Application Ser. No. 60/626,488, filed Nov. 10, 2004, each of which are incorporated herein by reference in their entirety.

FIELD OF THE INVENTION

This invention relates to methods and devices for registering an anatomical region with images of the anatomical region, verifying registration of an anatomical region, and dynamically referencing the anatomical region.

BACKGROUND OF THE INVENTION

Image Guided Surgery (IGS), also known as "frameless stereotaxy" has been used for many years to precisely locate and position therapeutic or medical measurement devices in the human body. Proper localization including position and orientation of these devices is critical to obtain the best result and patient outcome.

Some image guided surgery techniques use an externally placed locating device, such as a camera system or magnetic field generator together with an instrument containing a trackable component or "position indicating element" that can be localized by a locating device or tracking system (collectively referred to hereinafter a "tracking device"). These position indicating elements are associated with a coordinate system and are typically attached to instruments such as surgical probes, drills, microscopes, needles, X-ray machines, etc. and to the patient. The spatial coordinates and often the orientation (depending on the technology used) of the coordinate system associated with the position indicating elements can be determined by the tracking device in the fixed coordinate system (or fixed "frame of reference") of the tracking device. Many tracking devices may be able to track multiple position indicating elements simultaneously in their fixed frame of reference. Through geometrical transformations, it is possible to determine the position and orientation of any position indicating element relative to a frame of reference of any other position indicating element.

A variety of different tracking devices exist, having different advantages and disadvantages over each other. For example, optical tracking devices may be constructed to enable the highly accurate position and orientation of a tool equipped with position indicating elements to be calculated. However, these optical tracking devices suffer from line-of-site constraints, among other things. Electromagnetic (EM) tracking devices do not require a line-of-sight between the tracking device and the position indicating elements. Electromagnetic tracking devices may therefore be used with flexible instruments where the position indicating elements are placed at the tip of the instruments. One disadvantage, however, is that electromagnetic tracking devices are subject to interference from ferromagnetic materials and conductors. This interference may degrade accuracy when such ferromagnetic materials or conductors are placed in the proximity of position indicating elements or EM tracking devices. Other known tracking devices include, but are not limited to, fiber optic devices, ultrasonic devices and global positioning ("time of flight") devices.

By combining data obtained from a tracking device and a position indicating element with preoperative or intraoperative scans (such as for example, x-rays, ultrasounds, fluoroscopy, computerized tomographic (CT) scans, multislice CT scans, magnetic resonance imaging (MRI) scanning, positron emission tomographic (PET) scans, isocentric fluoroscope images, rotational fluoroscopic reconstructions, intravascular ultrasound (IVUS) images, single photon emission computer tomographer (SPECT) systems, or other images), it is possible to graphically superimpose the location of the position indicating element (and thus any surgical instrument having a position indicating element) over the images. This enables the surgeon to perform an intervention/procedure more accurately since the surgeon is better able to locate or orient the instrument during the procedure. It also enables the surgeon to perform all or part of the procedure without the need for additional x-rays or other images, but instead to rely on previously acquired data. This not only reduces the amount of ionizing radiation the surgeon and patient are exposed to, but can speed the procedure and enable the use of higher fidelity images than can not normally be acquired intra-operatively. Surgical plans may also be annotated onto these images (or indeed used without the images) to be used as templates to guide medical procedures.

Image Guided Surgery can be most effectively performed only if an accurate "registration" is available to mathematically map the position data of position indicating elements expressed in terms of the coordinate system of the tracking device, i.e., "patient space," to the coordinate system of the externally imaged data, i.e., "image space" determined at the time the images were taken. In rigid objects such as the skull or bones, one method of registration is performed by using a probe equipped with position indicating elements (therefore, the probe itself is tracked by a tracking device) to touch fiducial markers (such as, for example, small steel balls (x-spots) made by the Beekley Corporation, Bristol, Conn.) placed on the patient to obtain the patient space coordinates of the fiducials. These same fiducials are visible on an image such as, for example, a CT scan and are identified in the image space by indicating them, for example, on a computer display. Once these same markers are identified in both spaces, a registration transformation or equivalent mathematical construction can be calculated. In one commonly used form, a registration transformation may be a 4.times.4 matrix that embodies the translations, magnification factors and rotations required to bring the markers (and thus the coordinate systems) in one space in to coincidence with the same markers in the another space.

Fiducial markers used for registration can be applied to objects such as bone screws or stick-on markers that are visible to the selected imaging device, or can be implicit, such as unambiguous parts of the patient anatomy. These anatomical fiducials might include unusually shaped bones, osteophytes or other bony prominence, features on vessels or other natural lumens (such as bifurcations), individual sulci of the brain, or other markers that can be unambiguously identified in the image and patient. A rigid affine transformation such as the 4.times.4 matrix described above may require the identification of at least three non-collinear points in the image space and the patient space. Often, many more points are used and a best-fit may be used to optimize the registration. It is normally desirable that fiducials remain fixed relative to the anatomy from the time of imaging until the time that registration is complete.

Registration for image-guided surgery may be done by different methods. Paired-point registration is described above and is accomplished by a user identifying points in image space and then obtaining the coordinates of the corresponding points in patient space. Another type of registration, surface registration, can be done in combination with, or independent of, paired point registration. In surface registration, a cloud of points is digitized in the patient space and matched with a surface model of the same region in image space. A best-fit transformation relating one surface to the other may then be calculated. In another type of registration, repeat-fixation devices may be used that involve a user repeatedly removing and replacing a device in known relation to the patient or image fiducials of the patient.

Automatic registration may also be done. Automatic registration may, for example, make use of predefined fiducial arrays or "fiducial shapes" that are readily identifiable in image space by a computer. The patient space position and orientation of these arrays may be inferred through the use of a position indicating element fixed to the fiducial array. Other registration methods also exist, including methods that attempt to register non-rigid objects generally through image processing means.

Registrations may also be performed to calculate transformations between separately acquired images. This may be done by identifying "mutual information" (e.g., the same fiducial markers existing in each space). In this way, information visible in one image, but not the other, may be coalesced into a combined image containing information from both. In the same manner, two different tracking devices may be registered together to extend the range of a tracking device or to increase its accuracy.

Following registration, the two spaces (patient and image) are linked through the transformation calculations. Once registered, the position and orientation of a tracked probe placed anywhere in the registered region can be related to, for example, a scan of the region. Typically the tracking device may be connected to a computer system. Scans may also be loaded onto the computer system. The computer system display may take the form of a graphical representation of a probe or instrument's position superimposed onto preoperative image data. Accordingly, it is possible to obtain information about the object being probed as well as the instrument's position and orientation relative to the object that is not immediately visible to the surgeon. The information displayed can also be accurately and quantitatively measured enabling the surgeon to carry out a preoperative plan more accurately.

An additional concept in image guided surgery is that of "dynamic referencing." Dynamic referencing can account for any bulk motion of the anatomy relative to the tracking device. This may entail additional, position indicating elements, or other techniques. For example, in cranial surgery, position indicating elements that form the dynamic reference are often attached directly to the head or more typically to a clamp meant to immobilize the head. In spine surgery, for example, a dynamic reference attached (via a temporary clamp or screw) to the vertebral body undergoing therapy is used to account for respiratory motion, iatrogentic (e.g., doctor-induced) motion caused by the procedure itself, as well as motion of the tracking device. In an analogous manner, the tracking device itself may be attached directly to the anatomy, moving with the anatomy when it moves. For example, a small camera may be attached to a head-clamp so that movement of the head would produce movement of the camera, thus preserving registration.

"Gating" may also be used to account for motion of the anatomy. Instead of continually compensating for motion through dynamic referencing, "gated measurements" are measurements that are only accepted at particular instants in time. Gating has been used in, for example, cardiac motion studies. Gating synchronizes a measured movement (e.g., heartbeat, respiration, or other motion) to the start of the measurement in order to eliminate the motion. Measurements are only accepted at specific instants. For example, gating during image guided surgery of the spine may mean that the position of a tracked instrument may be sampled briefly only during peak inspiration times of a respiratory cycle.

Both registration and use of an image guided surgery system in the presence of anatomical motion (such as that which occurs during normal respiration) is generally regarded as safer and more accurate if a dynamic reference device is attached prior to registration (and/or if gating is used). Instead of reporting the position and orientation of a position indicating element of a tracked instrument in the fixed coordinate system of the tracking device, the position and orientation of the position indicating element of the tracked instrument is reported relative to the dynamic reference's internal coordinate system. Any motion experienced mutually by both the dynamic reference and the tracked instrument is "cancelled out."

There are many difficulties and problems in image guided surgery and the prior techniques. These are not limited to, but include: (a) obtaining adequate registration and (b) adequately dynamically referencing the anatomy or a portion thereof, and (c) verifying that registration is accurate enough to perform the procedure using image guidance.

Paired-point registration in rigid or near-rigid anatomical objects can be accomplished using direct probing. Paired-point registration is less-attractive when the anatomical object is either inaccessible, non-rigid, or both. When the anatomical object is not accessible but rigid (such as pelvic bone), it may be necessary to either palpate the surface of the object through probing through an opening in the skin, or through the rigid attachment of a palpatable registration object prior to imaging. In rigid and non-rigid organs or anatomically connected regions, methods such as ultrasound and laser surface scanning are used with varying amounts of success.

Registration and referencing of non-rigid and/or moving organs such as the liver, gall bladder, stomach, pancreas, kidney, lung, colon, heart, prostate gland, etc. is a difficult task. Use of devices such as probes generally deform the organ. Furthermore, it is difficult to attach any kind of dynamic reference to a soft moving object. Such organs tend to be generally inaccessible directly through the skin without damaging intervening tissue or the organ itself. Techniques using ultrasound are complicated by different sound velocities and attenuation from different tissues.

Current registration and dynamic referencing techniques usually assume that the tracked organ is rigid. Newer techniques are being proposed that are not limited to rigid organs. These can benefit from placement of multiple dynamic references. However, problems still exist since multiple dynamic references must be temporarily fixed to a deformable anatomical object.

Another limitation of current dynamic referencing techniques stems from the use of reference sensors. The most widely used method of referencing known in the art is to place a single, rigid, six degree-of-freedom (6 DOF), trackable device onto the organ of interest. This is typically screwed, clamped or otherwise rigidly attached to the organ of interest. Such rigid bodies are typically of large footprint, and give information only at the location to which they are attached. In the event that they are attached some distance from the site of intervention/procedure, or attached to a non-rigid object, the motion of the dynamic reference may not accurately track the motion at the site of intervention/procedure.

Another limitation of current image guided surgery techniques may include the difficulty of verifying that a registration has been performed correctly. Before proceeding to navigate the anatomical region of the patient based on preoperative images and registration, it may be important to ensure that the registration is accurate. In image guided procedures in hard tissue, a probe can be touched onto hard surfaces or features (after registration) to ensure the registration is accurate. This technique suffers from the same issues as registration itself in soft tissue, e.g., deformation of soft tissue during verification, access to the tissue, paucity of verification landmarks, and other problems.

A further limitation of current approaches is the amount of fluoroscopy that must be used to correctly position the therapy device in the event that image guided surgery is not used. While it does provide accurate and direct information of the progress of the intervention, images are two-dimensional in nature and require continuous exposure of the patient and surgical team to ionizing radiation. Three-dimensional images may be more useful.

These and other problems exist.

SUMMARY OF THE INVENTION

The invention addresses these and other problems by providing systems and methods for registration of an anatomical region of a patient, verification of the registration of the anatomical region, and dynamic referencing of the anatomical region.

As used herein, an anatomical region of a patient may include one or more organs, tissues, systems, cavities, and/or other regions (including regions having soft tissue and/or deformable bodies) of a human being or other animal. In one embodiment, the invention may use a conduit within the anatomical region to, inter alia, aid in providing image information and position information from within the anatomical region. This conduit may supply sufficient coordinate information regarding the anatomical region to be used for registration of the anatomical region. For example, a coronary artery surrounding the heart may provide sufficient topographical coordinate information regarding the heart to be used as a conduit for registration by a method of the invention.

In one embodiment, a conduit as used herein may include a naturally existing conduit within the anatomical region such as, for example, an artery, vein, or other vessel of the circulatory system or other naturally occurring conduit existing within the anatomical region of interest. In some embodiments, an "artificial conduit" may be created within the anatomical region such as, for example, a percutaneous puncture of tissue within the anatomical region by a cannula such as might be caused by a hypodermic needle. The process of insertion of this cannula may, in turn, form an artificial conduit within the anatomical region.

In other embodiments, a conduit may include a manufactured conduit that may be placed within the anatomical region such as, for example, a tube, a catheter, hollow endoscope, a tubular vascular guidewire, or other manufactured conduit that may be inserted into the anatomical region of interest. In some embodiments, a manufactured conduit and a naturally existing or artificial conduit may be used together. In some embodiments, a manufactured conduit may be inserted within an anatomical region to fill and/or conform to the dimensions of a space within that anatomical region. For example, a catheter or other conduit may be fed into a cavity within an anatomical region, such that the catheter coils, bends, folds, or otherwise "balls up" (without obstructing any lumens therein) inside the cavity, thus at least partially filling the volume of, or conforming to the dimensions of, the cavity. The methods described herein may then be performed using the catheter as it exists within the cavity.

In some embodiments, artificial conduits may used in conjunction with natural conduits and/or manufactured conduits. For example, an artificial conduit may be created (e.g., with a needle) in certain tissue (e.g., skin, connective tissue, or other tissue) to reach a natural conduit within the anatomical region (e.g., vein) or to insert a manufactured conduit (e.g., catheter).

In one embodiment, the invention provides a registration device for registration of an anatomical region of a patient. The registration device may include a tube, catheter, vascular guidewire, or other device that may be inserted into a conduit within the anatomical region to be registered. In some embodiments, the registration device may be constructed of a torqued bundle of metal filars or a helical wound spring with a central, large empty lumen that can accommodate one or more position indicating elements, detectable elements, wires, and/or other elements.

In some embodiments, the registration device may be freely slidable in within a conduit. In some embodiments, the registration device may be temporarily fixed within a conduit using one or more fixating elements such as, for example, balloons, deployable hooks, cages, stiffening wires, vacuum ports, or other elements.

In one embodiment, the registration device may include at least one position indicating element. The position indicating element may include an element whose location, position, orientation, and/or coordinates relative to a tracking device may be determined and recorded. As such, the position of the position indicating element within the conduit, and thus the position of at least one point of the conduit within the anatomical region of the patient, may be determined. The position indicating element may include, for example, a coil that may produce a magnetic field that is detectable by an electromagnetic tracking device. Other types of position indicating elements and/or tracking devices may be used.

In some embodiments, the registration device may include one or more features typically found in guidewires used in medical procedures such as, for example, a tapered tip, a hydrophilic coating (or other type of coating), safety or torque transmission, stiffening and/or support structures, metal filar tube windings (such as, for example, a helical spring winding, braided or twisted filars etc.), or other elements. In some embodiments, the distal tip portion of the registration device may contain malleable material, enabling the shape of the tip to be manually adjusted during a medical procedure. In some embodiments, the distal tip of the registration device may be closed or may contain a plug to prevent material seeping into the device.

In one embodiment, the position indicating element may be located at or near the tip of the registration device. In other embodiments, multiple position indicating elements may be located at various points along the length of registration device.

In one embodiment, the invention provides a method for registration of an anatomical region of a patient. One or more images of the anatomical region of the patient and/or the conduit within the anatomical region may be obtained by an imaging device. An imaging device may include, for example, an x-ray device or other imaging device. Position information regarding the path of the conduit within the anatomical region may then be obtained in the frame of reference of the image(s) (i.e., the path of the conduit in "image space").

In one embodiment the spatial pathway of the conduit in the frame of reference of the patient (i.e., in the "patient space") may be obtained. In one embodiment, this spatial pathway (or position information) may be obtained via a registration device that is inserted into the conduit, wherein the registration device includes at least one position indicating element. In one embodiment, the position indicating element may be located the distal tip of the registration device. A tracking device may sample the coordinates of the position indicating element included within the registration device as the inserted registration device is moved within the conduit, resulting in position information regarding the path of the conduit within the anatomical region in the frame of reference of the tracking device (this may also be referred to as the frame of reference of the patient, i.e., the "patient space"). In one embodiment, the movement of the registration device may include withdrawing the inserted registration device from the conduit.

In one embodiment, a registration transformation may then be calculated and the image data (e.g., information from the image space) of the anatomical region and the position data (information from the patient space) of the path of the conduit within the anatomical region may be mapped together (or "registered"), using the registration transformation. In some embodiments a registration transformation may include a registration transformation matrix or other suitable representation of the registration transformation. An exemplary registration transformation calculation method is known as singular valued decomposition (SVD) in which the same point locations are identified in each coordinate system (e.g., the image space and the patient space). Other registration transformations may be used.

In one embodiment, registration or mapping may be performed by bringing the coordinates of the anatomical region derived from the image data (the image space) into coincidence with the coordinates of the conduit within the anatomical region derived from the tracking device/position indicating element (the patient space). In some embodiments, additional coordinate sets may also be "co-registered" with the image and tracking device data. For example, a magnetic resonance image dataset may be first co-registered with a computerized tomography dataset (both image space), which may in turn be registered to the path of the conduit in the frame of reference of the patient (patient space).

The result of mapping the image space data and the patient space data together may include or enable accurate graphical representations (e.g., on the original image data) of an instrument or other tool equipped with a position indicating element through the anatomical region. In some embodiments, this navigation may enable image guided surgery or other medical procedures to be performed in/on the anatomical region.

In one embodiment, the invention provides a method for verifying registration of an anatomical region. In one embodiment, an image of an anatomical region of interest may be acquired using an imaging device. This anatomical region may include or be equipped with one or more conduits. A registration of the anatomical region may then be performed. This registration may use the methods described herein or may use other methods. In performing this registration, a registration transformation such as, for example, a registration transformation matrix, may be calculated.

One or more position indicating elements may then be placed into the anatomical region of interest. These position indicating elements may be different from those used for registration. As such, they may also be referred to as verification position indicating elements. Placement of the one or more position indicating elements may utilize a conduit within the anatomical region. In one embodiment, the one or more position indicating elements may be placed within the anatomical region of interest using a verification device. The verification device may include a tube, a catheter, vascular guidewire, or other device having one or more position indicating elements attached to it.

The position of the one or more position indicating elements may then be sampled by a tracking device. This position information may be combined with the previously mentioned registration. This combination may produce an "overlay image" or "composite image" where the image space positions of the one or more position indicating elements are calculated and displayed on the previously acquired image (or other image) of the anatomical region. Graphical icons representing the location and/or orientation of the one or more position indicating elements within the anatomical region may be displayed in the overlay or composite image. This location and/or orientation may be determined by the combined registration transformation and the coordinate of the one or more position indicating elements as sampled by the tracking device.

In some embodiments, the one or more position indicating elements may be moved within the anatomical region as their positions are sampled by the tracking device. The transformed location (as calculated using the registration transformation) of the one or more position indicating elements as they are moved may be displayed on the image. Errors in the registration may be indicated by movement of the one or more position indicating elements outside of the registered path within the anatomical region (e.g., such as outside a conduit registered within the anatomical region). The absence of errors may used to verify the registration.

In one embodiment, another method of verification of registration of an anatomical region may be performed and may be used together or separately from the verification method described above. In this method, one or more position indicating devices (such as those included in a verification device described above) may be placed into an anatomical region of a patient by way of, for example, a conduit within the anatomical region. The location of the one or more position indicating elements within the anatomical region may then be imaged using an imaging device such as, for example an x-ray device or other imaging device. The visualized location of the position indicating elements within the anatomical region may then be compared to points within the anatomical region as obtained by a registration. Discrepancies between the images of the position indicating elements and the points obtained by the registration may be indicative of errors in the registration.

In another embodiment, if the verification device includes one or more position indicating elements, at least one of which resides at the distal tip of the verification device, an image of the one or more position indicating elements as they are moved within the conduit may be taken over a period of time, thus, producing an image of the path if the conduit within the anatomical region. This may be compared to points within the anatomical region obtained by the registration for verification purposes.

In one embodiment, the invention provides a referencing device for dynamic referencing of an anatomical region of a patient. The referencing device may be or include a tube, a catheter, a vascular guidewire, or similar object that may be inserted into a conduit within the anatomical region to be referenced.

In one embodiment, the referencing device may be freely slidable in the conduit, and may be inserted into or removed from the conduit. In some embodiments, the referencing device may be fixed or held within the conduit by one or more restraining devices such as, for example, a balloon, vacuum ports along its length, deployable hooks, cages, stiffening wires, or other restraining devices. During and following registration procedures with which the referencing device is used, the referencing device may be held fixed relative to the anatomical region.

The referencing device may include one or more position indicating elements along its length. In some embodiments, these position indicating elements may be different from the position indicating elements used for other purposes, as such, they may also be referred to as referencing position indicating elements. The position indicating elements may enable the location, position, orientation, and/or coordinates of one or more points of reference of the referencing device to be detected by a tracking device as they exist within the fixed frame of reference of the tracking device. As such, the position indicating elements may enable detection of the location, position, orientation, coordinates and/or motion over time of one or more points of reference within an anatomical region of a patient.

In some embodiments, the referencing device or other element of the invention may contain a pressure sensor, an electromyograph (EMG) sensor, an electrocardiograph (ECG) sensor, or other devices or sensors, which may be used to gate the sampling of the reference sensors, to measure blood pressure, air pressure, or other quality.

In one embodiment, the invention provides a method for using referencing device to dynamically reference an anatomical region of a patient. In one embodiment, a referencing device having one or more position indicating elements may be inserted into one or more conduits within the anatomical region of interest. The spatial relationships (e.g., position, orientation) of the one or more position indicating elements relative to one another and/or relative to the anatomical region may then be determined via the tracking device or by other method. These spatial relationship measurements may by used to form a tracking model, such as a rigid body model (discussed above), piecewise rigid body representation, or deformable model of the anatomical region.

Any movement affecting the conduit within the anatomical region of interest may be detected via its effect on the one or more position indicating elements. This motion may include any motion that affects the contents of the anatomical region of interest such as, for example, a heartbeat, breathing, voluntary or involuntary movement by the patient, movement of the soft or deformable organs or tissues within the anatomical region due to intervention by a medical professional or instrument, gross movement of the body of the patient, or other movement. This movement may be monitored for by monitoring the position of the position indicating elements using the tracking device.

In one embodiment, the information provided by the position indicating elements may be used together with the model of the anatomical region to determine the motion of the anatomical region. This "model of motion" may be used to account for the motion of the anatomical region. In one embodiment, the model of motion may be used to adjust a registration of the anatomical region so as to account for, in real time, any movement affecting the anatomical region. In another embodiment, the model of motion may be used to adjust coordinates reported by the position indicating elements attached to an instrument in the anatomical region so as to account for, in real time, any movement affecting the anatomical region. In another embodiment, the model of motion may be used to form a local coordinate system in the vicinity of an instrument containing position indicating elements within the anatomical region. The model of motion may also be used to adjust the position of this local coordinate system. If the position indicating elements attached to the instrument are expressed in terms of this local coordinate system, it may be possible to account for, in real time, any movement affecting the anatomical region. Thus, re-registration need not be performed to account for movement affecting the anatomical region.

In some embodiments, the invention may include a computer-implemented integrated system ("integrated system") for performing one or more of the methods described herein (as well as other methods such as, for example, therapeutic, diagnostic, or other methods) and utilizing the apparatus described herein (as well as other apparatus). In one embodiment, an integrated system according to the invention may include a computer element. The computer element may include a processor, a memory device, a power source, a control application, one or more software modules, one or more inputs/outputs, a display device, a user input device, and/or other elements. The computer element may receive, send, store, and/or manipulate any data necessary to perform the processes described herein (including performing any calculations) or necessary for the function of the elements described herein.

According one embodiment, the computer element may host a control application. The control application may comprise a computer application which may enable one or more software modules.

In some embodiments, the one or more software modules may enable the processor to receive, send, and/or manipulate imaging data regarding the location, position, and/or coordinates of one or more instruments, devices, detectable elements, position indicating elements, or other elements of the invention inside an anatomical region of a patient. In some embodiments, the one or more software modules may also enable the processor to receive, send, and/or manipulate data regarding the location, position, and/or coordinates of one or more position indicating elements or other elements of the invention inside the anatomical region of the patient.

In some embodiments, the one or more software modules may also enable the processor to calculate one or more registration transformations, perform registration of coordinates from two or more coordinate systems according to the one or more transformation calculations, and produce one or more images from registered data. In some embodiments, images produced from image data, position data, registration data, other data, or any combination thereof may be displayed on the display device.

In some embodiments, the one or more software modules may enable the processor to receive, send, and/or manipulate data regarding the location, orientation, position, and/or coordinates of one or more position indicating elements for use in constructing a rigid-body description of an anatomical region of a patient. In some embodiments, the one or more software modules may enable the processor to create a dynamic, deformable model of the anatomical region of the patient, and display real time images regarding the anatomical region. In some embodiments, these images may be displayed on display the device.

In some embodiments, the integrated system may include a registration device. In one embodiment data may be sent and received between the registration device and computer element. The registration device may, inter alia, aid in providing image data, location data, position data, and/or coordinate data regarding an anatomical region of the patient or one or more elements of the invention within the anatomical region of the patient. The registration device may otherwise enable registration of the anatomical region the patient, (including soft tissues and/or deformable bodies).

In some embodiments, the integrated system may include a referencing device. In some embodiments data may be sent and received between the referencing device and computer element. The referencing device may, inter alia, aid in providing image data, location data, position data, coordinate data, and/or motion data regarding an anatomical region of the patient. The referencing device may otherwise enable dynamic referencing of an anatomical region of a patient, (including soft tissues and/or deformable bodies).

In one embodiment, the integrated system may include a tracking device. The tracking device may include an electromagnetic tracking device, global positioning system (GPS) enabled tracking device, an ultrasonic tracking device, a fiber-optic tracking device, an optical tracking device, a radar tracking device, or other type of tracking device. The tracking device may be used to obtain data regarding the three-dimensional location, position, coordinates, and/or other information regarding one or more position indicating elements within an anatomical region of the patient. The tracking device may provide this data/information to the computer element.

In one embodiment, the integrated system may include an imaging device. The imaging device may send and receive data from the integrated system. In one embodiment, the imaging device may be used to obtain image data, position data, or other data necessary for enabling the apparatus and processes described herein. The imaging device may provide this data to the computer element. The imaging device may include x-ray equipment, computerized tomography (CT) equipment, positron emission tomography (PET) equipment, magnetic resonance imaging (MRI) equipment, fluoroscopy equipment, ultrasound equipment, an isocentric fluoroscopic device, a rotational fluoroscopic reconstruction system, a multislice computerized tomography device, an intravascular ultrasound imager, a single photon emission computer tomographer, a magnetic resonance imaging device, or other imaging/scanning equipment Other devices and or elements such as, for example, temperature sensors, pressure sensors, motion sensors, electrical sensors, EMG equipment, ECG equipment, or other equipment or sensors may be part of or send and receive data from the integrated system.

Those having skill in the art will appreciate that the invention described herein may work with various system configurations. Accordingly, more or less of the aforementioned system components may be used and/or combined in various embodiments. It should also be understood that various software modules and control application that are used to accomplish the functionalities described herein may be maintained on one or more of the components of system recited herein, as necessary, including those within individual tools or devices. In other embodiments, as would be appreciated, the functionalities described herein may be implemented in various combinations of hardware and/or firmware, in addition to, or instead of, software.

The various objects, features, and advantages of the invention will be apparent through the detailed description of the preferred embodiments and the drawings attached hereto. It is also to be understood that the following detailed description is exemplary and not restrictive of the scope of the invention.

DETAILED DESCRIPTION OF PREFERRED EMBODIMENTS

Figure 1A:
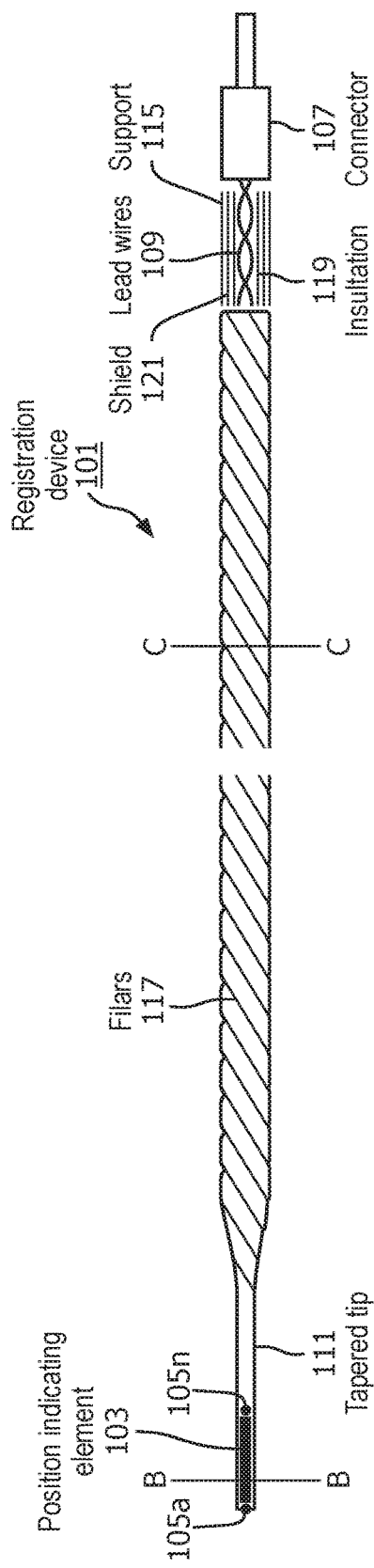
FIG. 1A is an exemplary diagram of a registration device according to an embodiment of the invention.

The invention provides systems and methods for registration of an anatomical region of a patient, verification of the registration of the anatomical region, and dynamic referencing of the anatomical region, wherein the anatomical region may include soft tissue and/or deformable bodies.

In one embodiment, the invention may use a conduit within an anatomical region of a patient to, inter alia, aid in providing image information and position information from within the anatomical region. This conduit may supply sufficient coordinate information regarding the anatomical region to be used for registration of the anatomical region. For example, a coronary artery surrounding the heart may provide sufficient topographical coordinate information regarding the heart to be used as a conduit for registration by a method of the invention.

In one embodiment, a conduit as used herein may include a naturally existing conduit within the anatomical region such as, for example, an artery, vein, or other vessel of the circulatory system; a bronchial tube or other vessel of the respiratory system; a vessel of the lymphatic system; an intestine or other vessel of the digestive system; a urinary tract vessel; a cerebrospinal fluid vessel; a reproductive vessel; an auditory vessel; a cranial ventricle; an otolaryngological vessel; or other naturally occurring conduit existing within the anatomical region of interest.

In some embodiments, an "artificial conduit" may be created within the anatomical region such as, for example, a percutaneous puncture of tissue within the anatomical region by a cannula such as might be caused by a hypodermic needle. The process of insertion of this cannula may, in turn, form an artificial conduit within the anatomical region.

In other embodiments, a conduit may include a manufactured conduit that may be placed within the anatomical region such as, for example, a tube, a catheter, hollow endoscope, a tubular vascular guidewire, or other manufactured conduit that may be inserted into the anatomical region of interest. In some embodiments, a manufactured conduit and a naturally existing or artificial conduit may be used together. For example, a catheter, cannula, or tube may be navigated inside a naturally existing vessel of the anatomical region. In some embodiments, a first manufactured conduit may be inserted within a second manufactured conduit, which may in turn be inserted into the anatomical region, an artificial conduit within the anatomical region, or within a naturally existing conduit within the anatomical region.

In some embodiments, a manufactured conduit may be inserted within an anatomical region to at least partially fill and/or conform to the dimensions of a space within that anatomical region. For example, a catheter or other conduit may be fed into a cavity within an anatomical region, such that the catheter coils, bends, folds, or otherwise "balls up" (without obstructing any lumens therein) inside the cavity, thus at least partially filling the volume of, or conforming to the dimensions of, the cavity. The methods described herein may then be performed using the catheter as it exists within the cavity.

In some embodiments, artificial conduits may used in conjunction with natural conduits and/or manufactured conduits (described below). For example, an artificial conduit may be created (e.g., with a needle) in certain tissue (e.g., skin, connective tissue, or other tissue) to reach a natural conduit within the anatomical region (e.g., vein) or to insert a manufactured conduit (e.g., catheter).

In one embodiment, the invention provides a registration device for registration of an anatomical region of a patient. As described below, the registration device may be part of, or be operatively connected to, an integrated system for registration, verification of registration, dynamic referencing, navigation, and/or other functions (hereinafter "integrated system"), which is described in detail below.

Figure 1C:
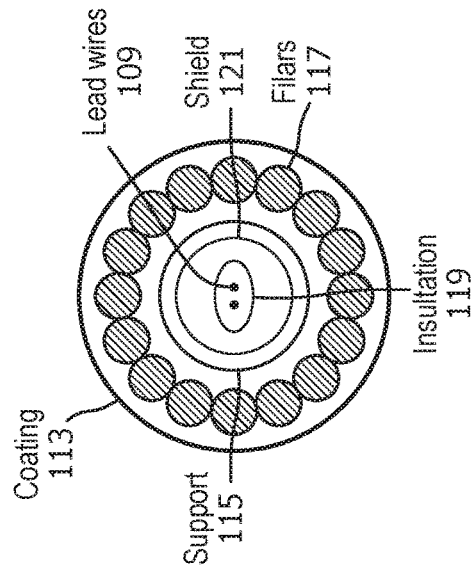
FIG. 1C is an exemplary diagram of a registration device according to an embodiment of the invention.
Figure 1B:
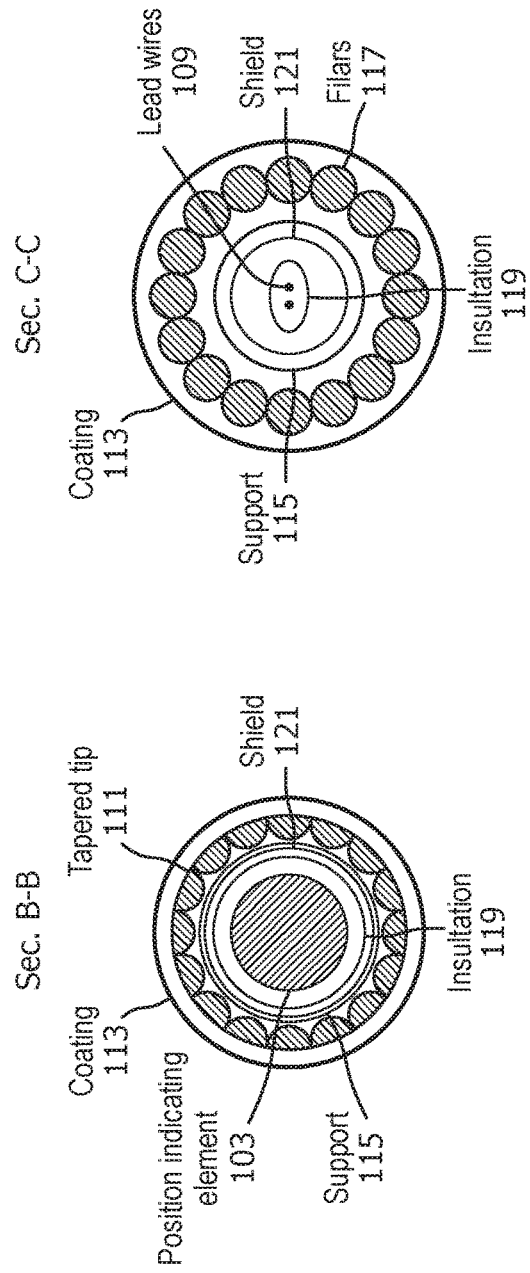
FIG. 1B is an exemplary diagram of a registration device according to an embodiment of the invention.

FIGS. 1A-1C illustrate a registration device 101 according to an embodiment of the invention. Registration device 101 may include a tube, catheter, vascular guidewire, or other device that may be inserted into a conduit within the anatomical region to be registered. In some embodiments, registration device 101 may be constructed of a torqued bundle of metal filars or a helical wound spring with a central, large empty lumen that can accommodate one or more position indicating elements, detectable elements, wires, and/or other elements. In one embodiment, registration device 101 may be similar to the design of the "act-one" from ASAHI INTECC Co., LTD of Japan.

In some embodiments, registration device 101 may be freely slidable in within a conduit. In some embodiments, registration device 101 may be temporarily fixed within a conduit using one or more fixating elements such as, for example, balloons, deployable hooks, cages, stiffening wires, or other elements.

In one embodiment, registration device 101 may include at least one position indicating element 103. Position indicating element 103 may include an element whose location, position, orientation, and/or coordinates relative to a tracking device may be determined and recorded. As such, the position of position indicating element 103 within the conduit, and thus the position of at least one point of the conduit within the anatomical region of the patient, may be determined. Position indicating element 103 may include a device whose position may be detectable by a tracking device in the frame of reference of the tracking device. For example, position indicating element 103 may include a coil that may produce a magnetic field that is detectable by an electromagnetic tracking device. In one embodiment, position indicating element 103 may include a coil that detects a magnetic field emitted by the electromagnetic tracking device. In some embodiments position indicating elements and their position in the frame of reference of a tracking device may be enabled by "Hall Effect" transducers or superconducting quantum interference devices (SQUID). In other embodiments, position indicating element 103 may include an element whose position is detectable by a global positioning system (GPS) enabled tracking device, an ultrasonic tracking device, a fiber-optic tracking device (e.g., Shape-Tape, MEasurand, Inc., Fredricton, New Bruswick), an optical tracking device, or a radar tracking device. Other types of position indicating elements and/or tracking devices may be used. In one embodiment, the tracking device used to detect the position of position indicating element 103 may be part of, or operatively connected to, an integrated system.

In one embodiment, registration device 101 may include lead wires 109 extending from position indicating element 103 back through the device to electrical connections 107. Electrical connections 107 may include contacts that may be flush with, or smaller than, the outer diameter of registration device 101. Electrical connections 107 may also include, for example, a plug, contact bands, or other connections. Electrical connections 107 may facilitate measurement of the position of one or more position indicating elements 103 and connection of registration device 101 to a tracking system, an integrated system, and/or other computer-implemented system.

In one embodiment, lead wires 109 may be shielded to prevent electromagnetic interference. Shielding of lead wires 109 may involve electrical shielding 121. In one embodiment, lead wires 109 may be encased in an insulating tube placed inside of the registration device 101 or otherwise insulated by electrical insulation 119. In some embodiments, lead wires 109 may be embedded in a tube such as that made by the Phelps Dodge company which includes conductors embedded in the walls of the tube. Alternatively, lead wires 109 may be conductors placed within a filar bundle that makes up the wall of the tube itself (as is known in the art).

Registration device 101 may contain one or more detectable elements 105a-105n. In one embodiment, detectable elements 105a-105n may be placed on or adjacent to position indicating element 103, such that the location of detectable elements 105a-105n may be correlated to the location and/or orientation of position indicating element 103 as disclosed in U.S. Pat. No. 6,785,571, which is incorporated herein by reference in its entirety. Detectable elements 105a-105n may include radio-opaque elements or elements that are otherwise detectable to certain imaging modalities such as, for example, x-ray, ultrasound, fluoroscopy, computerized tomography (CT) scans, positron emission tomography (PET) scans, magnetic resonance imaging (MRI), or other imaging devices. Detectable elements 105a-105n may enable the detection and/or visualization of certain points of reference of registration device 101 within a conduit residing in an anatomical region of a patient, which may aid in registration, verification of registration, dynamic referencing, navigation, and/or other uses.

In some embodiments, registration device 101 may include one or more features typically found in guidewires used in medical procedures such as, for example, a tapered tip 111, a hydrophilic coating 113 (or other type of coating), safety or torque transmission, stiffening and/or support structures 115, metal filar tube windings 117 (such as, for example, a helical spring winding, braided or twisted filars etc.), or other elements.

In some embodiments, the distal portion of registration device 101 may comprise a floppy portion with bending stiffness less than the rest of the device. A floppy, bendable tip may enable registration device 101 to be navigated into hard-to-reach, arborized paths, which may not otherwise be possible without a floppy tip. This may be accomplished by grinding the exterior of registration device 101 to reduce its bending stiffness, or otherwise changing the material properties of the tip in another manner. In some embodiments, the distal tip portion of registration device 101 may contain a pre-bent section, which may be bent from approximately 15 to 120 degrees to assist in navigating an anatomical region. In some embodiments, the distal tip of registration device 101 may take on complex shapes such as, for example, a "J" shape, or other shapes. In some embodiments, the distal tip portion of registration device 101 may contain malleable material, enabling the shape of the tip to be manually adjusted during a medical procedure. In some embodiments, the distal tip of registration device 101 may be closed or may contain a plug to prevent material seeping into the device.

In one embodiment, position indicating element 103 may be located at or near the tip of registration device 101. In other embodiments, multiple position indicating elements may be located at various points along the length of registration device 101.

FIG. 1B illustrates a cross-section of registration device 101 according to an embodiment of the invention as viewed from line segment B-B of FIG. 1A. FIG. 1C illustrates a cross section of registration device 101 according to an embodiment of the invention as viewed from line segment C-C of FIG. 1A. FIGS. 1A-1C are exemplary only. One of skill in the art would appreciate that registration device 101 may include alternate configurations, some or all of the components discussed herein, and/or additional components.

Figure 2:
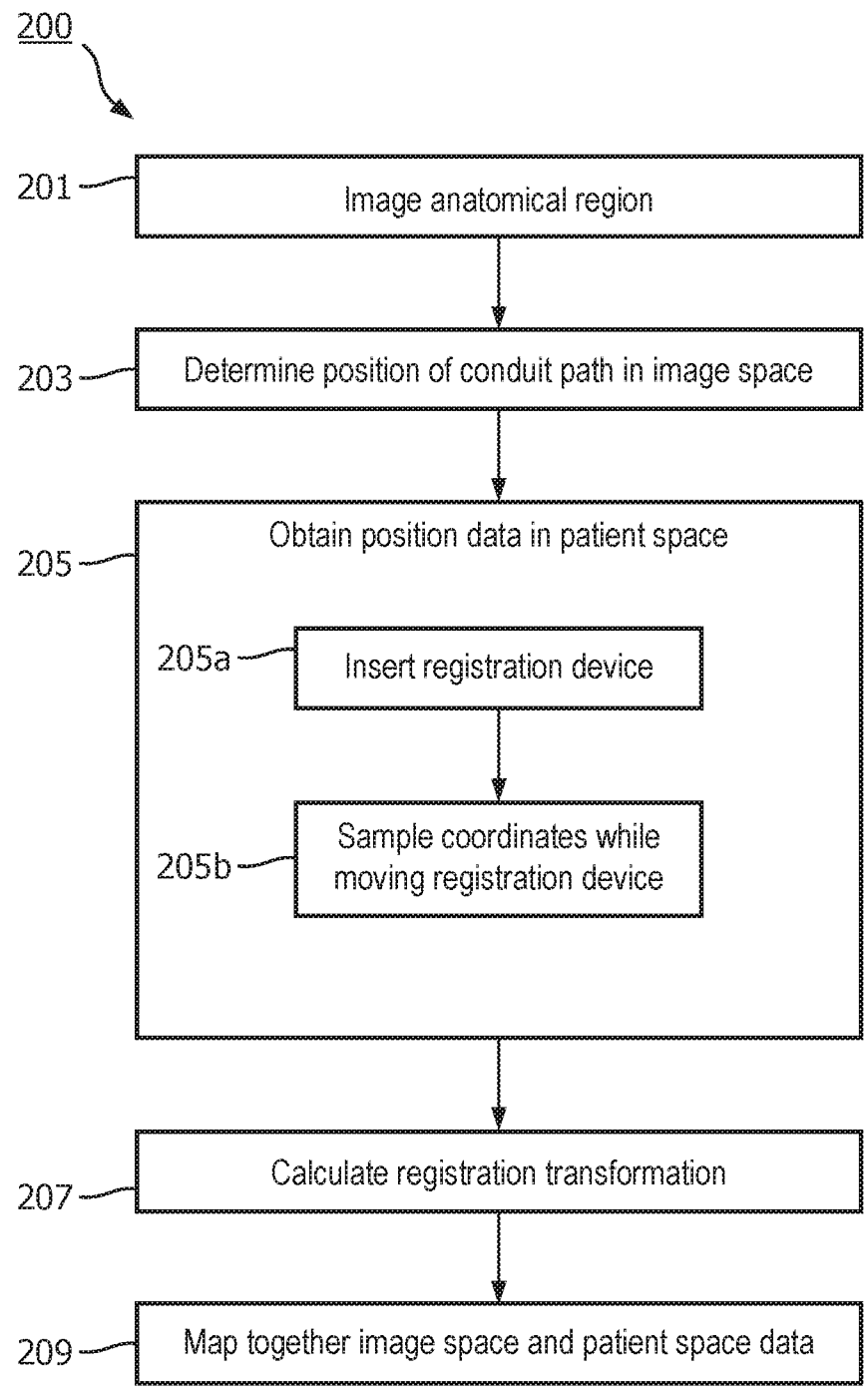
FIG. 2 is an exemplary process of registration of an anatomical region according to an embodiment of the invention.

FIG. 2 illustrates an exemplary process 200 according to an embodiment of the invention, wherein registration of an anatomical region of a patient may be performed. In an operation 201, one or more images of the anatomical region of the patient and/or the conduit within the anatomical region may be obtained by an imaging device. An imaging device may include, for example, an x-ray device, an ultrasound device, a fluoroscopic device, a computerized tomography (CT) device, a positron emission tomography (PET) device, a magnetic resonance imaging (MRI) device, an isocentric fluoroscope, a rotational fluoroscopic reconstruction system, a multislice computerized tomography device, an intravascular ultrasound imager, a single photon emission computer tomographer, or other imaging device. In some embodiments, the imaging device may be part of, connected to, and/or exchange data with an integrated system.

In an operation 203, position information regarding the path of the conduit within the anatomical region may be obtained in the frame of reference of the image(s) taken in operation 201 (i.e., the path of the conduit in "image space"). In one embodiment, the path of the conduit may be obtained through a segmentation process in which the images are examined for the conduit and connected regions within the images (that are identified as the conduit) may be coalesced to determine the spatial pathway of the conduit in the coordinate system of the images. Several such methods are known in the art such as, for example, those outlined by L. M. Lorigo in Lorigo et al., CURVES: Curve Evolution for Vessel Segmentation, 5 Medical Image Analysis 195-206 (2001).

In an operation 205, the spatial pathway of the conduit in the frame of reference of the patient (i.e., in the "patient space") may be obtained. In one embodiment, this spatial pathway (or "position data") may be obtained via a registration device (similar to, or the same as, registration device 101 of FIG. 1) that is inserted into the conduit, wherein the registration device includes at least one position indicating element.

In one embodiment, the registration device may contain a position indicating element at its tip. In an operation 205a, the registration device may be inserted into the conduit within in the anatomical region of the patient. In an operation 205b, the tracking device may then sample the coordinates of the position indicating element included within the registration device as the registration device is moved within the conduit, resulting in position information regarding the path of the conduit within the anatomical region in the frame of reference of the tracking device (this may also be referred to as the frame of reference of the patient, i.e., the "patient space").

In other embodiments, the registration device may contain multiple position indicating elements along its length. In these embodiments, the registration device may be inserted into the conduit within the anatomical region of the patient. The coordinates of the multiple position indicating elements may then be detected by a tracking device while the position indicating elements are either moved or kept stationary within the conduit, resulting in position information regarding the path of the conduit within the anatomical region in the frame of reference of the tracking device (i.e., the patient space). In one embodiment, if the registration device contains multiple position indicating elements and their coordinates are sampled within the conduit as the conduit is moving (e.g., movement affecting the anatomical region that in turn affects the conduit), enhanced tempero-spatial information regarding the movement of the patient space may be obtained.

In an operation 207, a registration transformation may be calculated. In some embodiments a registration transformation may include a registration transformation matrix or other suitable representation of the registration transformation.

A transformation is a mathematical tool that relates coordinates from one coordinate system to coordinates from another coordinate system. There may be multiple methods to calculate the registration transformation. One exemplary registration transformation calculation method may include "brute force" approach. A brute force approach may involve treating the pre-registration image data and the registration position data as completely independent datasets and manually attempting to match the two datasets by altering each translation, rotation, and scaling parameter in turn to create the best match. This however, may be inefficient.

Another exemplary method may include an Iterative Closest Point (ICP) algorithm, one version of which is described in U.S. Pat. No. 5,715,166, which is incorporated herein by reference in its entirety.

Another exemplary registration transformation calculation method is known as singular valued decomposition (SVD) in which the same point locations are identified in each coordinate system (e.g., the image space and the patient space).

In an operation 209, the image information of the anatomical region (image space) and the position information of the path of the conduit within the anatomical region (patient space) may be registered or mapped together using the registration transformation. The registration or mapping may be performed by bringing the coordinates of the anatomical region derived from the image data (the image space) into coincidence with the coordinates of the conduit within the anatomical region derived from the tracking device/position indicating element (the patient space). In some embodiments, additional coordinate sets may also be "co-registered" with the image and tracking device data. For example, a magnetic resonance image dataset may be first co-registered with a computerized tomography dataset (both image space), which may in turn be registered to the path of the conduit in the frame of reference of the patient (patient space).

The result of mapping the image space data and the patient space data together may include or enable accurate graphical representations (e.g., on the original image data, surgical plan or other representation) of an instrument or other tool equipped with a position indicating element through the anatomical region. In some embodiments, this navigation may enable image guided surgery or other medical procedures to be performed in/on the anatomical region.

For example, following registration, instruments such as needles, probes, flexible endoscopes, stents, coils, drills, ultrasound transducers, pressure sensors, or indeed any flexible or rigid instrument that is equipped with a position determining element, may be navigated into the anatomical region where the registration occurred (in particular, near the conduit or regions immediately adjacent to it). In one embodiment, images of the anatomical region embellished with icons representing the instrument location and orientation as it is moved may be enabled.

Figure 3:
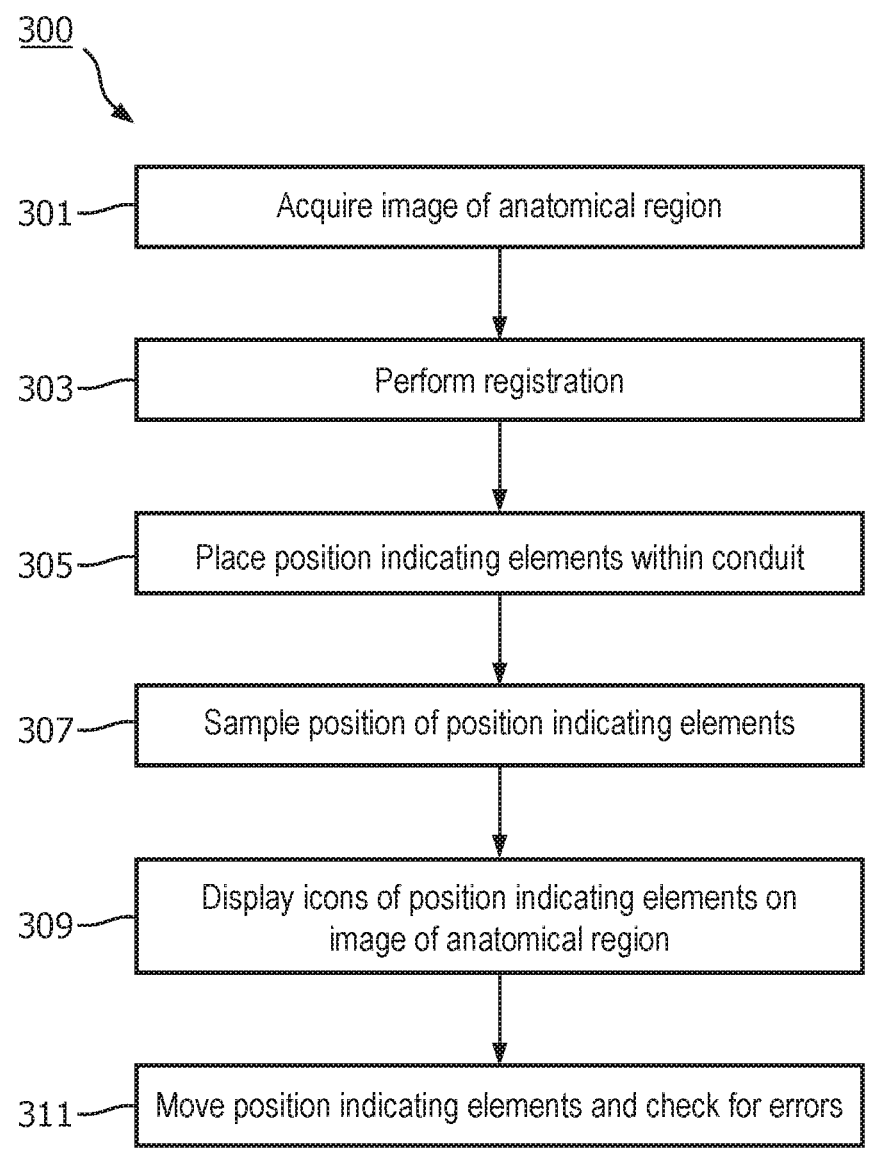
FIG. 3 is an exemplary process for verification of registration of an anatomical region according to an embodiment of the invention.

In one embodiment, the invention provides a method for verifying registration of an anatomical region. FIG. 3 illustrates an exemplary process 300 according to an embodiment of the invention, wherein registration of an anatomical region may be verified. In an operation 301, an image of an anatomical region of interest may be acquired using an imaging device. This anatomical region may include or be equipped with one or more conduits. In an operation 303, a registration of the anatomical region may be performed. This registration may use the methods described herein or may use other methods. In performing this registration a registration transformation such as, for example, a registration transformation matrix, may be calculated.

In an operation 305, one or more position indicating elements may be placed into the anatomical region of interest. Placement of the one or more position indicating elements may utilize a conduit within the anatomical region. In one embodiment, one or more position indicating elements may be placed within the anatomical region of interest using a verification device. The verification device may include a tube, a catheter, vascular guidewire, or other device having one or more position indicating elements attached to it. In one embodiment, the verification device may be the same as or similar to registration device 101 of FIG. 1.

In an operation 307, the position of the one or more position indicating elements may be sampled by a tracking device. This position information may be combined with the registration of operation 303. This combination may produce an "overlay image" or "composite image" where the image space positions of the one or more position indicating elements are calculated and displayed on the image acquired in operation 301. In an operation 309, graphical icons representing the location and/or orientation of the one or more position indicating elements in the anatomical region may be displayed in the overlay or composite image. This location and/or orientation may be determined by the combined registration transformation and the coordinates of the one or more position indicating elements as sampled by the tracking device in operation 307.

In an operation 311, the one or more position indicating elements may be moved within the anatomical region as their positions are sampled by the tracking device. The transformed location (as calculated using the registration transformation of operation 307) of the one or more position indicating elements as they are moved may be displayed on the image. Errors in the registration may be indicated by movement of the one or more position indicating elements outside of the registered path within the anatomical region (e.g., such as outside a conduit registered within the anatomical region). The absence of errors may be used to verify the registration.

In one embodiment, another method of verification of registration of an anatomical region may be performed and may be used together or separately from the verification method described above. In this method, one or more position indicating devices (such as those included in a verification device described above) may be placed into an anatomical region of a patient by way of, for example, a conduit within the anatomical region. The location of the one or more position indicating elements within the anatomical region may then be imaged using an imaging device such as, for example an x-ray device, ultrasound device, fluoroscopy device, computerized tomography (CT) device, positron emission tomography (PET) device, magnetic resonance imaging (MRI), or other imaging device. The visualized location of the position indicating elements within the anatomical region may then be compared to points within the anatomical region as obtained by a registration. Discrepancies between the images of the position indicating elements and the points obtained by the registration may be indicative of errors in the registration. In one embodiment, this operation may be performed entirely numerically and automatically, e.g., through the use of a computer to compare the two paths.

In one embodiment, if the verification device includes multiple position indicating elements along its length, an image of the position indicating elements as they are positioned at a single point in time may be obtained. This image, as indicated above, may be compared to points within the anatomical region obtained by the registration for verification of the registration.

In another embodiment, if the verification device includes one or more position indicating elements, at least one of which resides at the distal tip of the verification device, an image of the one or more position indicating elements as they are moved within the conduit may be taken over a period of time, thus, producing an image of the path if the conduit within the anatomical region. This image may be compared to points within the anatomical region obtained by the registration for verification purposes.

In another embodiment, the verification device itself may comprise or be injected with a detectable material, such that an image of the verification device inserted into the conduit at a single point in time may produce an image of the path of the conduit within the anatomical region. This also may be compared to points within the anatomical region obtained by the registration for verification purposes.

Figure 4:
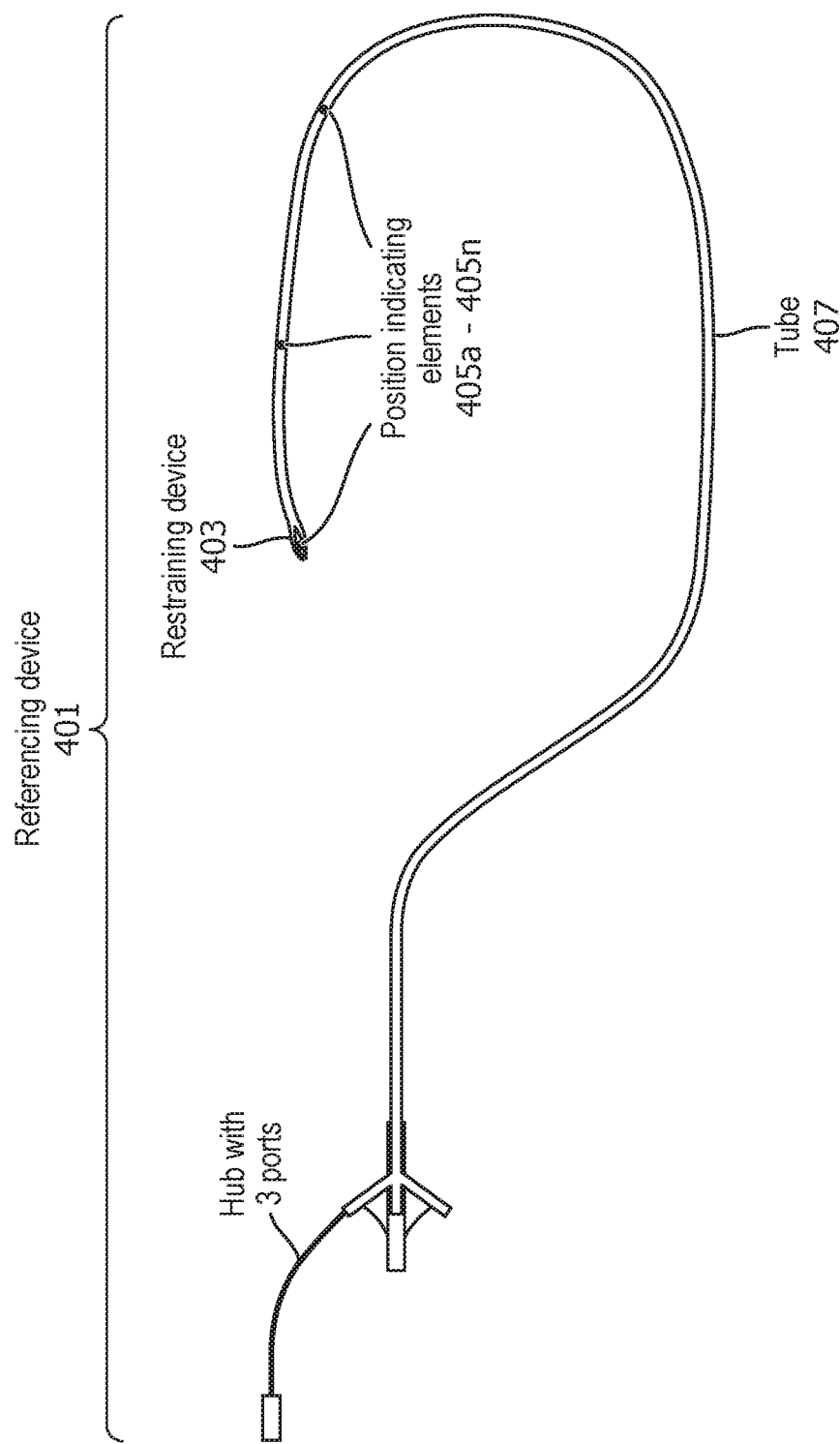
FIG. 4 is an exemplary diagram of a referencing device according to an embodiment of the invention.

In one embodiment, the invention provides a referencing device for dynamic referencing of an anatomical region of a patient. As described below, the referencing device may be part of, or be operatively connected to, an integrated system. In some embodiments, the components of a referencing device may be the same as, or similar to, registration device 101 of FIG. 1. FIG. 4 illustrates a referencing device 401 according to an embodiment of the invention. Referencing device 401 may be or include a tube, a catheter, a vascular guidewire, or similar object (referred to herein for convenience as tube 407) that may be inserted into a conduit within the anatomical region to be referenced.

In one embodiment, referencing device 401 may be freely slidable in the conduit, and may be inserted into or removed from the conduit. In some embodiments, referencing device 401 may be fixed or held within the conduit by one or more restraining devices 403 such as, for example, a balloon, vacuum ports along its length, deployable hooks, cages, stiffening wires, or other restraining devices. During and following registration procedures with which referencing device 401 is used, referencing device 401 may be held fixed relative to the anatomical region.

Referencing device 401 may include one or more position indicating elements 105a-405n along its length. Position indicating elements 405a-405n may enable the location, position, orientation, and/or coordinates of one or more points of reference of referencing device 401 to be detected by a tracking device as they exist within the fixed frame of reference of the tracking device. As such, position indicating elements 405a-405n may enable detection of the location, position, orientation, coordinates and/or motion over time of one or more points of reference within an anatomical region of a patient.

In one embodiment, a position indicating element 405 may include a device whose position may be detectable by a tracking device in the frame of reference of the tracking device. For example, a position indicating element 405 may include a coil that may produce a magnetic field that is detectable by an electromagnetic tracking device. In one embodiment, position indicating element 405 may include a coil that detects a magnetic field emitted by an electromagnetic tracking device. In some embodiments position indicating elements 405a-405n and their position in the frame of reference of a tracking device may be enabled by "Hall Effect" transducers or superconducting quantum interference devices (SQUID). In other embodiments, position indicating elements 405a-405n may include elements whose position is detectable by a global positioning system (GPS) enabled tracking device, an ultrasonic tracking device, a fiber-optic tracking device, an optical tracking device or a radar tracking device. Other types of position indicating elements and/or tracking devices may be used. In one embodiment, the tracking system used to detect the position of position indicating elements 405a-405n may be part of, or operatively connected to, an integrated system.

Referencing device 401 may include electrical wiring, electrical shielding, insulation, electrical connections, or other electrical elements such as those described with regard to registration device 101 of FIG. 1. These electrical components may enable the operation of one or more position indicating elements and/or the connection of the referencing device to an integrated system according to the invention. In some embodiments, the companion tracking device to position indicating elements 405a-405n (or other element of the invention) may be part of, connected to, and/or exchange data with an integrated system according to the invention.

In some embodiments, one or more of position indicating elements 405a-405n may be located along the length of referencing device 401. In some embodiments, referencing device 401 may be constructed so that the region surrounding one or more position indicating elements 403 does not bend. In some embodiments, one or more position indicating elements .sup.405a-405n may be encased in an insulating tube placed inside of referencing device 401.

In one embodiment, the outside of referencing device 401 (or other aspects of the invention) may include a lubricious and/or hydrophilic coating. In some embodiments, the distal portion of referencing device 401 may include a floppy portion with bending stiffness less than the rest of the device. This floppiness may be accomplished by grinding the exterior of the tube to reduce its bending stiffness or otherwise. In some embodiments, the distal tip of referencing device 401 may be closed or include a plug to prevent material seeping into the device. In some embodiments, referencing device 401 may include an intrinsic or shapeable curve.

Referencing device 401 or other element of the invention may contain a pressure sensor, an electromyograph (EMG) sensor, an electrocardiograph (ECG) sensor or other devices or sensors, which may be used to gate the sampling of the reference sensors, to measure blood pressure, air pressure, or other quality.

Figure 5:
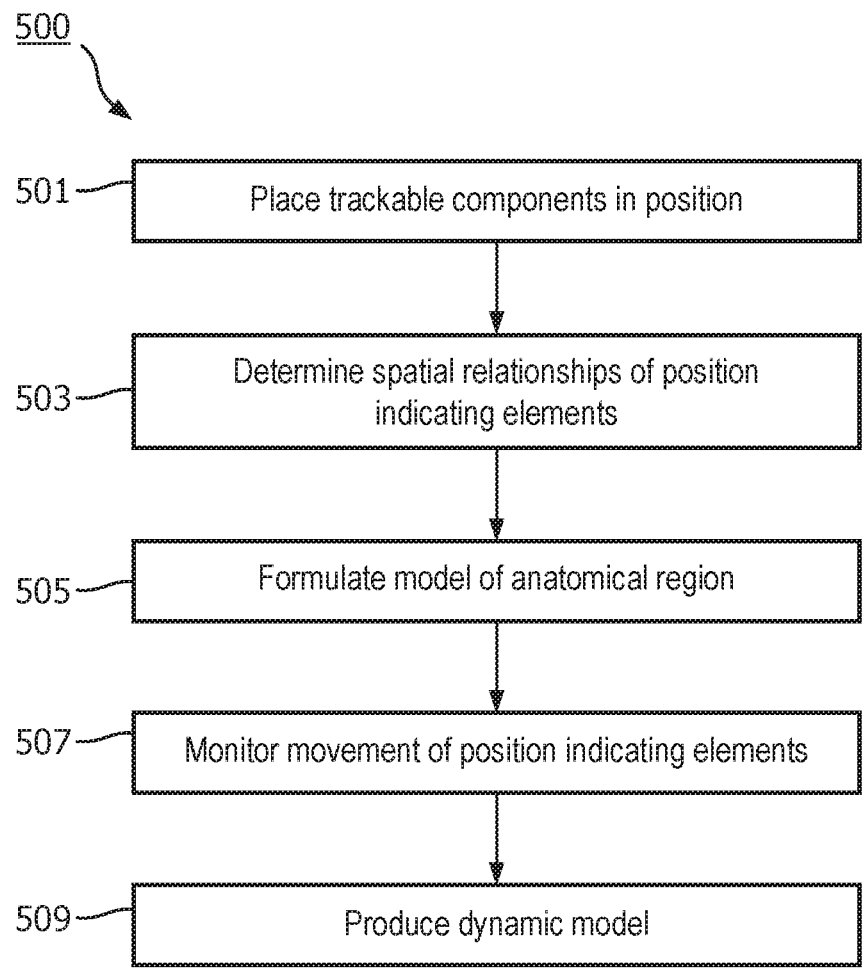
FIG. 5 is an exemplary process for dynamic referencing of an anatomical region according to an embodiment of the invention.

FIG. 5 illustrates an exemplary method 500 according to an embodiment of the invention wherein a referencing device may be used to dynamically reference an anatomical region of a patient. In an operation 501, a referencing device having one or more position indicating elements may be inserted into one or more conduits within the anatomical region of interest.

In some embodiments, it may be desirable to approximate or model the anatomical region as a rigid body (a "rigid body model"). In these cases, it may be desirable to utilize a device capable of resolving six degrees of freedom. In some embodiments, it may be desirable to use a registration device having position indicating elements that each measure less than six-degrees of freedom, as they may be simpler to manufacture, can generally be made smaller, and may have other advantages. To resolve six degrees of freedom where fewer than six degrees of freedom are measured by a single position indicating element, multiple position indicating elements may be utilized in combination. This may be best facilitated if the position indicating elements are in a known spatial relationship to one another.

As a priori spatial relationships between the position indicating elements may not be consistently known, it may be difficult to formulate the six degrees of freedom representation unless the spatial relationship between the position indicating elements can be determined. In one embodiment, this relationship may be determined by imaging the position indicating elements of the referencing device within the anatomical region to determine their relative location, position, and/or orientation and hence, their spatial relationship to one another. In one embodiment, one or more detectable elements detectable by an imaging device may exist on or near the position indicating elements of the referencing device to aid determination of this spatial relationship. In other embodiments the position indicating elements themselves may be detectable by an imaging device. In one embodiment, a tracking device may be placed in multiple relative locations to the position indicating elements, and the relative location of the position indicating elements may be calculated, enabling determination of a six degree of freedom representation of the position indicating elements.

In some embodiments, a subset or weighted combination of the position indicating elements may be used in the creation of a rigid body model of the anatomical region. In general, the position closest to an identified point of interest (e.g., where a medical procedure is to be performed) may be weighted higher than those distant in calculating the rigid body (some of which may be weighted at 0).

For certain anatomical regions having consistent or nearly consistent, repetitive predictable motion (e.g., heartbeat, breathing, or other motion), the motion in one part of the anatomical region may be inferred and modeled from a single point measurement.

In one embodiment, multiple rigid body models of the same region may be used. To construct these multiple rigid body models, the positions of different combinations of position indicating elements may detected be at different times. For example, in an embodiment where three position indicating elements are placed within an anatomical region, elements one and two may be detected at a certain point in time to form a first rigid body, elements one and three may be detected at a different point in time for form a second rigid body, and elements two and three may be detected at a third point in time to form a third rigid body. In some embodiments, the different points in time may be selected to correspond to movement affecting the anatomical region. In some embodiments, the points in time wherein the different combinations are detected may not be different. It will be understood to those skilled in the art that the number of position indicating elements may be more than three, as may be the number of points in time at which the positions of one or more combinations of position indicating elements are detected.

In one embodiment, the rigid body models used for dynamic referencing of that region may be modeled from different combinations of position indicating elements than an adjacent anatomical region. The rigid body model that is formed may thus be synchronized both spatially, and temporally with the anatomical region. A sensor, such as a pressure transducer, electrocardiogram monitor, or other sensor may be placed on the patient and used to measure phases of these cycles to assist with selection of the appropriate combination of position sensing elements.

In some embodiments, a rigid body model used to represent the motion of the anatomical region may be obtained by using least squares combination of data from all elements of the invention (imaging, registration, referencing, and/or other data) to create a rigid approximation of the anatomical region of interest (even if the anatomical region is deformable). The resulting approximation may be more accurate than, for example, selecting two position indicating elements as they exist in the anatomical region, and creating a rigid body based on them alone.

In other embodiments, a rigid body model may not be used to model the motion of the anatomical region. In these embodiments, the position indicating elements may be used to drive a finite element model or other non-rigid (deformable) model of the anatomical region by for example, acting as boundary conditions.

In an operation 503, the spatial relationships (e.g., position, orientation) of the one or more position indicating elements relative to one another and/or relative to the anatomical region may then be determined via an imaging device, the tracking device, and/or by other method. These spatial relationships may be determined by the methods discussed above. In an operation 505, these spatial relationship measurements may by used to form one or more models, such as a rigid body model (discussed above), piecewise rigid body representation, or deformable model of the anatomical region.

Any movement affecting the conduit within the anatomical region of interest may be detected via its effect on the one or more position indicating elements. This motion may include any motion that affects the contents of the anatomical region of interest such as, for example, a heartbeat, breathing, voluntary or involuntary movement by the patient, movement of the soft or deformable organs or tissues within the anatomical region due to intervention by a medical professional or instrument, gross movement of the body of the patient, or other movement. In an operation 507, this movement may be monitored for by monitoring the position of the position indicating elements using the tracking device.

In an operation 509, the information provided by the position indicating elements may be used together with the model of the anatomical region to determine the motion of the anatomical region. Operation 509 may produce a dynamic model of the anatomical region that models any motion affecting the anatomical region in real time. This "model of motion" may be used to account for the motion of the anatomical region. In one embodiment, the model of motion may be used to adjust a registration of the anatomical region so as to account for, in real time, any movement affecting the anatomical region. In another embodiment, the model of motion may be used to adjust coordinates reported by the position indicating elements attached to an instrument in the anatomical region so as to account for, in real time, any movement affecting the anatomical region. In another embodiment, the model of motion may be used to form a local coordinate system in the vicinity of an instrument containing position indicating elements within the anatomical region. The model of motion may also be used to adjust the position of this local coordinate system. If the position indicating elements attached to the instrument are expressed in terms of this local coordinate system, it may also be possible to account for, in real time, any movement affecting the anatomical region. Thus, re-registration need not be performed to account for movement affecting the anatomical region.

Figures 6A, 6B:
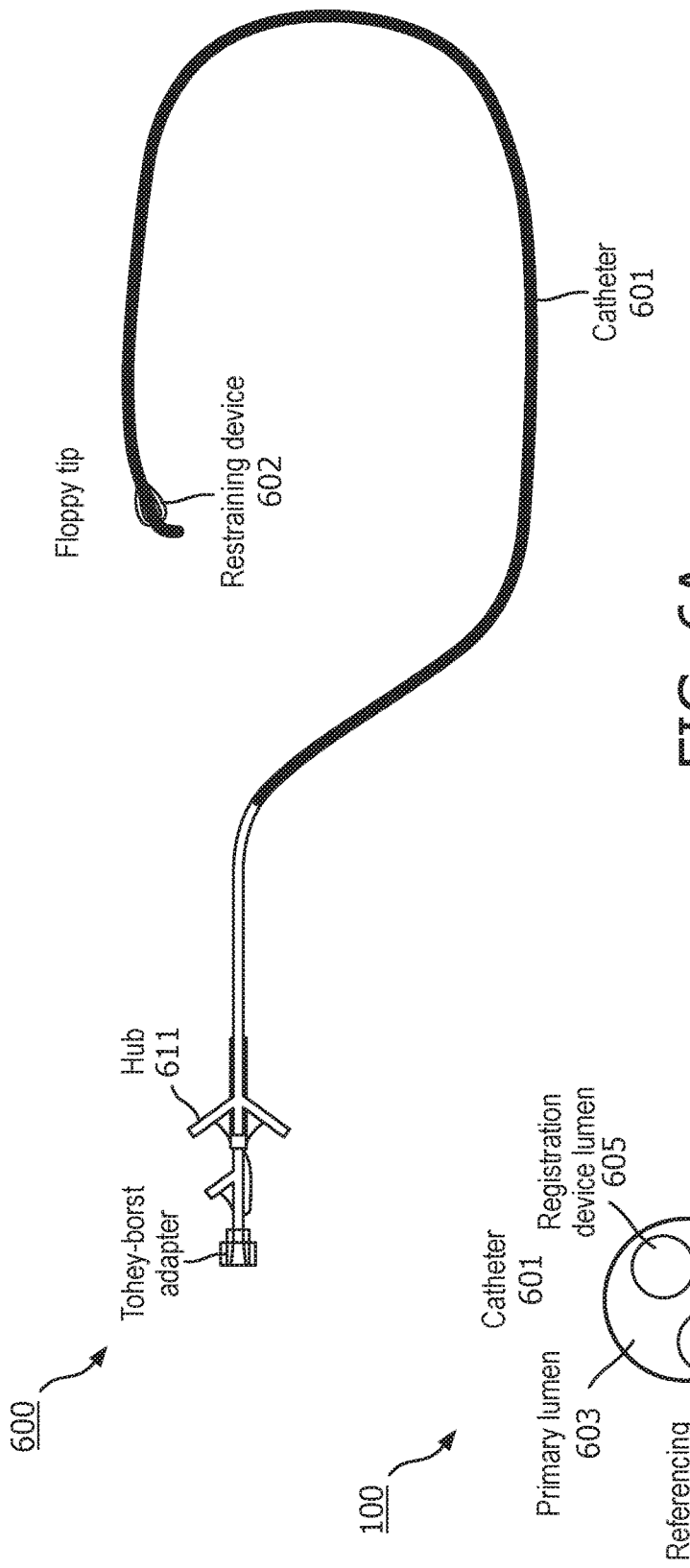
FIG. 6A is an exemplary diagram of an apparatus according to an embodiment of the invention.
FIG. 6B is an exemplary diagram of an apparatus according to an embodiment of the invention.

FIGS. 6A and 6B illustrate a device 600 that may be used, by itself or in conjunction with a naturally existing conduit to enable and/or aid the apparatus or processes described herein. In one embodiment, device 600 may include a tube, a catheter, or other conduit 601. For convenience, this embodiment will refer to a catheter 601. The invention is not so limited. Catheter 601 may have properties otherwise consistent with its use as described herein as would be apparent to those having ordinary skill in the art. In some embodiments, catheter 601 may comprise a material that does not mask other features of the invention otherwise detectable to imaging devices. In one embodiment, catheter 601 need not be independent, and could itself be a lumen or in a lumen within an endoscope such as a cystoscope, brochioscope, or other instrument.

In some embodiments, catheter 601 may include a primary lumen 603 that may accommodate one or more of a registration device, a verification device, a referencing device, a therapeutic instrument, an endoscope, a biopsy device, a brush, a guidewire, a tube for inflation or activation of fixation methods or members, a channel for injection of contrast agent, or other device. In some embodiments, catheter 601 may include two or more lumens, internal tubes, or channels. These lumens may each accommodate one or more of a registration device, a verification device a referencing device, a guidewire, a tube for inflation or activation of fixation methods or members, a channel for injection of contrast agent, a channel for deploying a therapeutic device (e.g., endoscope, ultrasound probe, etc.), or other elements. Some of these lumens may be shared by multiple devices/elements, if appropriate.

FIG. 6B illustrates a cross section of apparatus 600. In one embodiment, apparatus 600 may include one or more of a registration device lumen 605, a referencing device lumen 607, a contrast agent lumen 609, a lumen for other devices such as medical tools for performing an intervention and/or medical procedure (not otherwise indicated), and/or other lumens or channels. In some embodiments one or more of the aforementioned lumens may enable devices to be removably inserted into catheter 601 and freely slidable therein.

Contrast agent lumen 609 may enable the introduction of a radio-opaque (or otherwise detectable) contrast agent such as, for example, barium compounds or similar compounds. This contrast agent may enable the visualization of catheter 601 and/or the anatomical region near (or beyond) the distal end of catheter 601 by an imaging device.

In some embodiments, catheter 601 may include one or more restraining devices 602 for fixating itself within an anatomical region of a patient such as, for example, a balloon, deployable hooks, cages, stiffening wires, screws, hooks, vacuum devices, helical catheter arrangement, or other restraining devices.

In some embodiments, catheter 601 may include a hub 611 containing ports that can accommodate various wires and tubes described herein. Hub 611 may comprise various fittings depending on the number of lumens/capabilities of the catheter. For example, hubs used to insert a referencing device as described herein may include constructions capable of locking the referencing device in a particular position and sealing it from any fluid flow, if appropriate. Other hubs may be adaptable to attach multi-port valves for selecting a fluid source such as, for example, a contrast agent that may be injectable into catheter 601. Other hubs may be used, for example, those for handling wires, cables, electrical connections, or for other uses.

In some embodiments, catheter 601 may include one or more detectable elements and or position indicating elements along its length (not otherwise illustrated in FIG. 6). In some embodiments, detectable elements and/or position indicating elements included in/on catheter 601 may be used for preliminary positioning of catheter 601 in the anatomical region of the patient. In some embodiments, the detectable elements and/or position indicating elements may be used to enable catheter 601 itself to be used as a registration device, a verification device, a referencing device, and/or for other uses. In some embodiments, the detectable elements and/or position indicating elements may enable catheter 601 to serve as a secondary or backup device for registration, verification, and or dynamic registration (primary methods being performed by the devices described herein or by other devices).

While separate devices (e.g., catheter, referencing device, registration device, etc.) are described herein for performing various tasks (e.g., registration of an anatomical area of a patient, verification of registration, dynamic referencing of an anatomical region, contrast agent injection into an anatomical region, navigation within an anatomical region, or other tasks), it would be understood by one having skill in the art that a single device (e.g., catheter 101), when equipped with the proper subset of components (e.g., position indicating elements, detectable elements, lumens, guidewires, etc.) may be used to perform any subset or combination of the functions described herein. As such, in one embodiment of the invention, some or all of the features of the registration device, the verification device, and/or the referencing device may be included in a manufactured conduit (similar to or the same as catheter 601) to enable the apparatus or processes described herein.

In some embodiments, one or more of the devices and/or processes described herein may be used with each other in various combinations. FIGS. 7A-7G are exemplary illustrations according to an embodiment of the invention wherein a catheter 701, referencing device 709, and a registration device 713 may be used to perform registration and referencing of an anatomical region near a patient's heart 702. Those having ordinary skill in the art will realize that similar devices and techniques according to the invention may be used in the lung to map out pulmonary pathways, in the colon to map out parts of the digestive system, the urethra to map out the urinary system, or in other areas of the human or mammalian anatomy to map or image other areas.

Figure 7B:
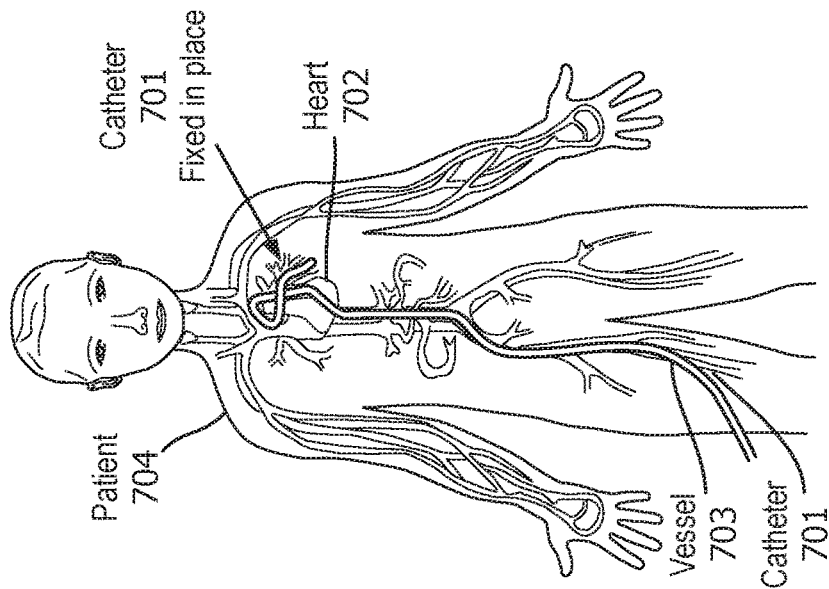
FIG. 7B is an exemplary diagram of an apparatus within an anatomical region of a patient according to an embodiment of the invention.
Figure 7A:
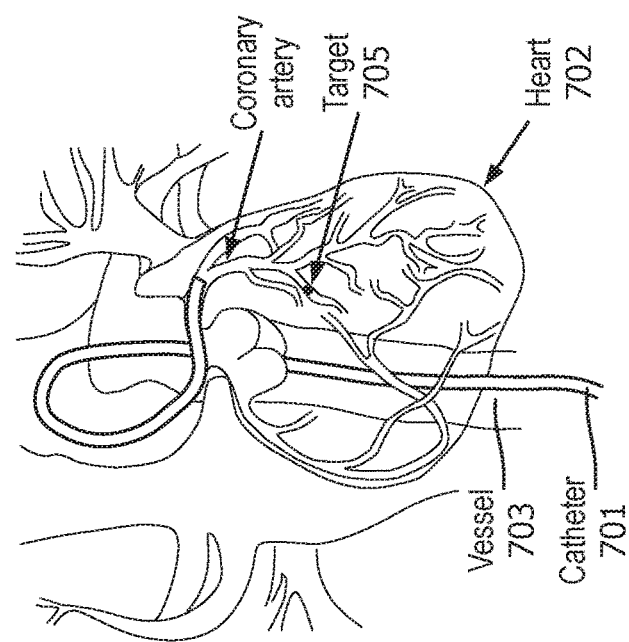
FIG. 7A is an exemplary diagram of an apparatus within an anatomical region of a patient according to an embodiment of the invention.

FIG. 7A, illustrates a catheter 701 (similar to or the same as catheter 601 of FIG. 6) or other hollow tube that may be introduced into a patient through an orifice of the patient (not otherwise illustrated) such as, for example, the mouth, the nose, the urethra, the anus, an incision into the circulatory system, a manufactured channel created during a surgical procedure, or other orifice (whether naturally existing or created) in the patient. FIG. 7B is an exemplary illustration according to an embodiment of the invention wherein catheter 701 is inserted into a vessel 703 of patient 704. Referring back to FIG. 7A, catheter 701 may be introduced through a portal, over a guidewire or any other method as known in the art. Catheter 701 may be introduced through an orifice into vessel 703 or region of the patient such as, for example the bronchial tree, the digestive tract, ventricles in the brain, the esophagus, the circulatory system, or other vessels or regions of the anatomy of the patient.

Catheter 701 may be placed using conventional techniques (e.g., fluoroscopy) to a position in the body. Target 705 is illustrated in FIG. 7A as a dark circle. Target 705 may include something of interest such as, for example, a stenosis, an aneurysm, a tumor, a polyp, a calcification, or other element or condition of interest. Is should be noted that because FIG. 7A is illustrative only, target 705 may not necessarily exist in the circulatory system but may exist in another anatomical region of the body. Additionally, target 705 need not exist in the precise anatomical system in which catheter 701 and other elements of the invention are placed, but may be nearby, such as a tumor present in the same or adjacent tissue to that being monitored by catheter 701.

Figure 7C:
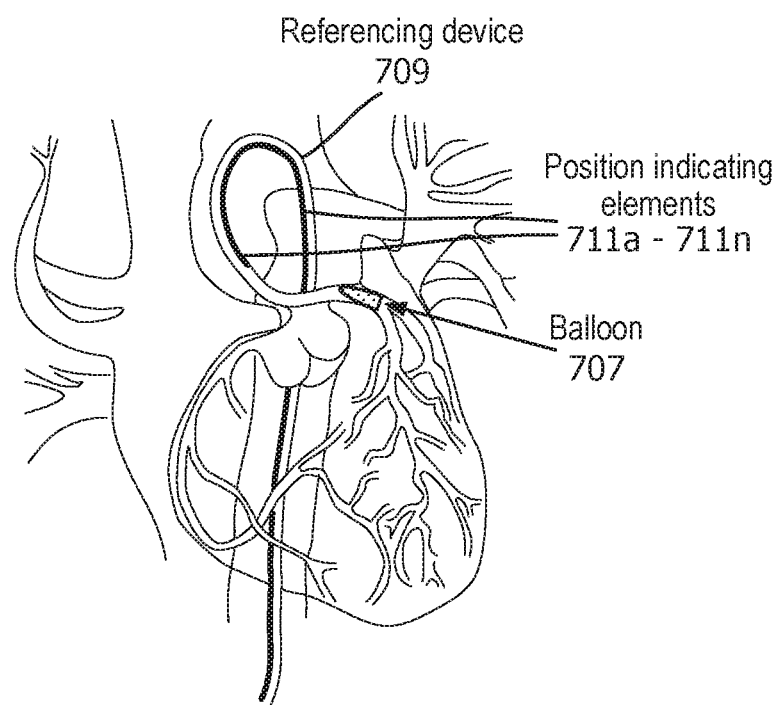
FIG. 7C is an exemplary diagram of an apparatus within an anatomical region of a patient according to an embodiment of the invention.

Catheter 701 may be fixed in place to prevent motion within vessel 703. FIG. 7C illustrates catheter 701 fixed in place in through the use of an inflatable member such as, for example, a balloon 707. In some embodiments, catheter 701 may be fixed using deployable cages, hooks, insertable stiffening wires, vacuum devices, helical catheter arrangement designed to maintain catheter location within an anatomical region or conduit therein, or other methods known in the art. In some embodiments, catheter 701 may be fixed at several locations or continuously along its length, not just the tip, so that it does not move independently of the anatomy or change its shape once placed.

FIG. 7C illustrates a referencing device 709 (similar to or the same as referencing device 401 of FIG. 4) may be inserted into a lumen of catheter 701 (if it is not already integrally present in the construction of catheter 701). Referencing device 709 may contain multiple position indicating elements 711a-71n, enabling position information of position indicating elements 711a-711n and ultimately, vessel 703 to be determined. In some embodiments, referencing device 709 may be placed elsewhere (such as another vessel) or omitted entirely and a different method of dynamic referencing used, or dynamic referencing not employed.

Once in embodiment, referencing device 709 may be fixed in place within catheter 701 so that it moves with the anatomy (which may be advantageous for performing dynamic referencing). If, for example, referencing device 709 is fixed or held stationary within catheter 701, and catheter 701 is fixed to and moves with the anatomy, then referencing device 709 may be able to move with the anatomy. If referencing device 709 is initially independent of catheter 701, deployable hooks, cages or balloons or other restraining devices (not otherwise illustrated) may be used to fix referencing device 709 in place.

Figure 7E:
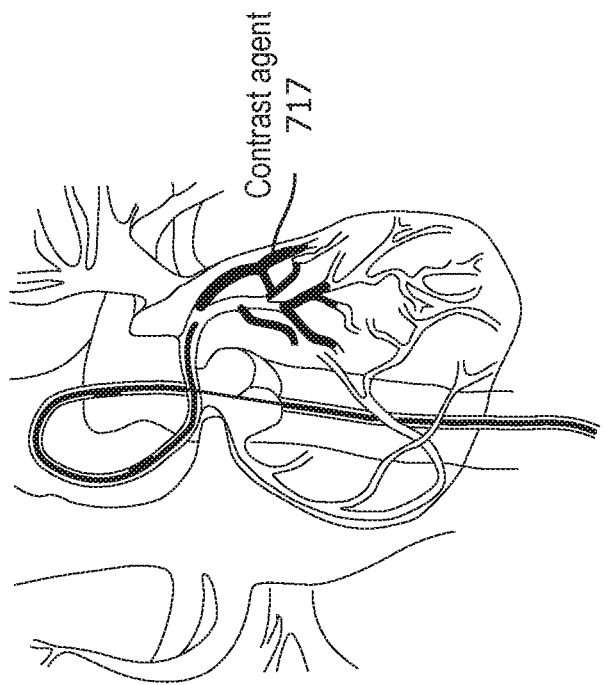
FIG. 7E is an exemplary diagram of an apparatus within an anatomical region of a patient according to an embodiment of the invention.
Figure 7D:
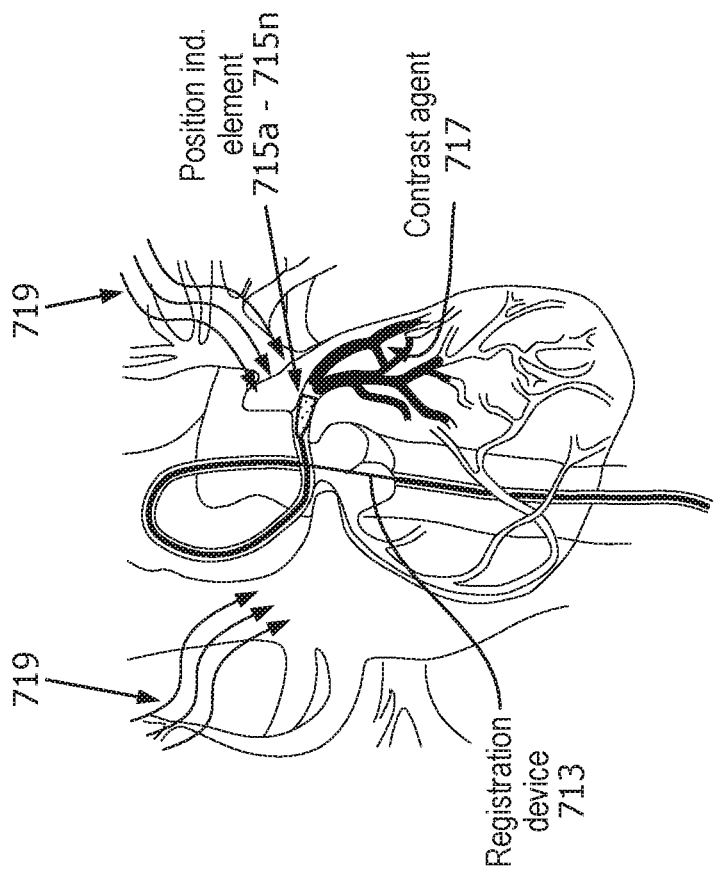
FIG. 7D is an exemplary diagram of an apparatus within an anatomical region of a patient according to an embodiment of the invention.

FIG. 7D illustrates a registration device 713 (similar to or the same as registration device 605 in FIG. 6 or registration device 101 in FIG. 1) that may be used to register the anatomical region. In some embodiments, registration device 713 may be positioned almost entirely within catheter 701. Registration device 713 may include at least one position indicating element 715 which may, in some embodiments, be located near the tip of registration device 713.

As described above, registration of an anatomical region may include imaging the anatomical region. In one embodiment, the imaging may include simultaneous or "coordinated" biplanar x-rays, or other methods of imaging. In some embodiments, in conjunction with imaging, a bolus of contrast agent 717 may be injected into catheter 701 so that catheter 701 is filled with contrast agent 717. In some embodiments, contrast agent 717 may include radio opaque or other detectable (by an imaging device) contrast agent such as, for example, a barium compound or other suitable agent. By way of example, in vascular surgery, a contrast agent containing a barium compound or a bolus of carbon dioxide gas is routinely injected into a catheter to visualize the vasculature in the vicinity of the tip of a catheter. In pulmonary surgery, a propyliodone or Xenon-133 mixture may be administered to the patient. FIG. 7D illustrates contrast agent 717 distal to the tip of catheter 701.

In some embodiments, the injection of contrast agent 717 into catheter 701 may have at least two effects: (1) it may render catheter 701 radio-opaque or otherwise detectable, so its path can be determined through an imaging device; and (2) excess contrast agent 717 may be directed out of the distal end of catheter 701 so that contrast agent 717 occupies the vessels, cavities, tissue, or other area surrounding catheter 701, enabling clear visualization image of the paths in the vicinity and beyond the tip of catheter 701. Without this contrast agent, these areas are not usually visible to an imaging modality. FIG. 7E is an exemplary illustration of the visualization that may be provided by introduction of contrast agent 717 into the distal vessels of the anatomical region of interest.

The second effect of introduction of contrast agent 717 into catheter 701 may also be achieved by injecting contrast agent 717 through a separate catheter, lumen, needle, or other method appropriate for the intervention being performed. The first effect may also be achieved by making registration device 713, catheter 701, or some component of catheter 701 from radio-opaque material so as to show the pathway of registration device 713.

While a similar result to the first and second effects of introducing a contrast agent into catheter 701 may be achieved by enhancing the whole anatomical vessel with contrast agent, it is generally desirable to inject as little contrast agent as possible into the anatomy of the patient, as: (a) these compounds tend to be nephrotoxic (toxic to the kidneys), so it is preferable to inject as little contrast as possible; (b) visualizing the path of catheter 701 alone would better reflect the precise path of a device contained within the catheter, since flooding a whole vessel or entire anatomical region with contrast agent, especially if a large or complex region is involved, lends inaccuracy to the actual path taken by an instrument (e.g., contrast agent may travel along areas not traveled by the instrument); and (c) the injection of contrast agent 717 may be easily facilitated in the local anatomical region near the distal end of the catheter and is more conducive to precise visualization beyond the catheter tip if required.

In one embodiment, the 2D anatomical region may be optionally co-registered with a preoperative image, where applicable. For example, if a pre-operative scan (e.g., MRI, arterial phase image, or other scan) were conducted and revealed a tumor or other lesion, the preoperative scan may be co-registered with an image taken for registration purposes prior to registration.

In some embodiments, during registration, a three dimensional path of the center of the registration device (the "centerline") may be calculated in the coordinate system of the previously obtained images of the anatomical region. In some embodiments, a three-dimensional (3D) map of the anatomical area of interest and/or the location of at least part of registration device 713 may be constructed during this calculation. Simultaneous biplane fluoroscopy (the rays of which are indicated as imaging waves 719), multi-slice CT, or other fast 3D image acquisition of the anatomical region may be used, in conjunction with images (those mentioned above or other images) of the anatomical region to construct the 3D map and/or the location of at least part of registration device 713. A 3D mathematical map of the structure and channels of the anatomical region to be navigated beyond the tip of catheter 701 may also be constructed using the images (those mentioned above or other images) or scan information of the anatomical region (particularly if a contrast agent 717 has been introduced therein). In some embodiments, the image data (e.g., the 3d model/map)

regarding the anatomical region and the conduit therein (e.g., vessel 705 and/or catheter 701) may be expressed as a 3D spline, parametric equations, voxels, polygons, coordinate lists, or other indicators of the walls or path of the component structures, or simply a "skeleton" of the central axis (centerline) of the component tubes and structures, existing in the coordinate system of the image devices.

Other surrounding areas of interest may also be incorporated into the map. In vascular surgery, for example, the 3D map may include the vessels enhanced at the end of the catheter showing the path to a stenosis or narrowing of one of the vessels.

The 3D map of registration device 713 within catheter 701 may be reconstructed from images of the contrast agent 717 constrained within catheter 701, from the image of catheter 701 itself, from images of registration device 713, and/or from other images or source of information regarding the 3D path. This 3D path may form the coordinates of the path of registration device 713 in the "image space" or coordinate system of the imaging device.

Figure 7G:
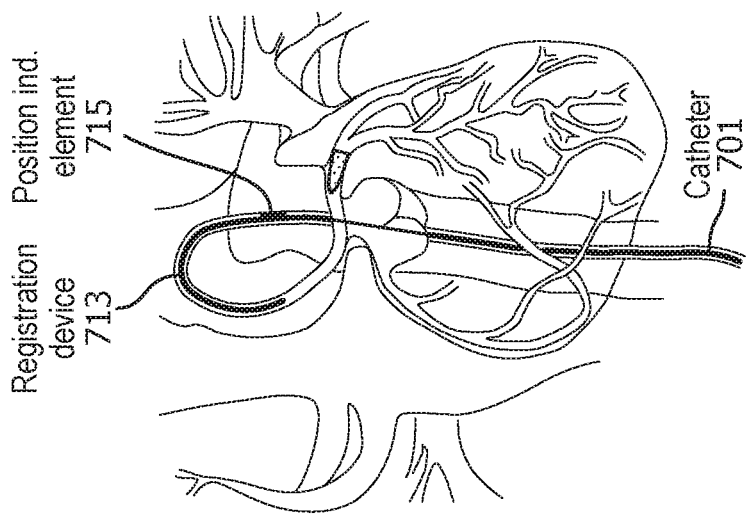
FIG. 7G is an exemplary diagram of an apparatus within an anatomical region of a patient according to an embodiment of the invention.
Figure 7F:
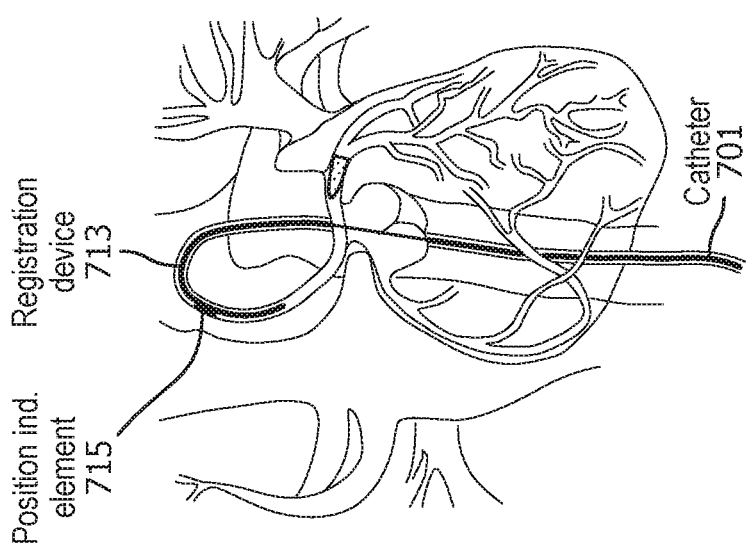
FIG. 7F is an exemplary diagram of an apparatus within an anatomical region of a patient according to an embodiment of the invention.

During registration of an anatomical region, a tracking device may be activated and the coordinates of registration device 713's path in a coordinate system of the tracking device (as indicated by position indicating element 715) or, the coordinates in the frame of reference of a coordinate system created by referencing device 709 (if used) may be determined. In some embodiments, this may be accomplished by sliding the registration device 713 through catheter 701 while a tracking device simultaneously samples the coordinates of position indicating element 715. This essentially retraces the image space path that had been visualized by the previous operations and provides a corresponding set of position data in the "patient space" or coordinate system of the tracking system. FIGS. 7F and 7G illustrate registration device 713 and position indicating element 715 being moved within catheter 701. The position data obtained by the tracking device may also be expressed as a 3D spline, parametric equations along the registration tube, coordinate lists, or other suitable formats.

A registration transformation may then be calculated. As noted herein, there may be multiple methods to calculate the registration transformation. In an exemplary registration transformation calculation method, the (x,y,z) positions may be parameterized as a function of distance along the path traveled by registration device 713. In one embodiment, at the start of position data collection, registration device 713 is located within catheter 701 at the time of imaging (e.g., x-ray and/or other imaging data) to determine its path (i.e., S(0)). As registration device 713 is moved within catheter 701, position indicating element 715 moves a distance, S(t), which can be estimated from the (x,y,z) position of position indicating element 715 using the incremental Euclidian distance, i.e. $\sqrt{(x_k-x_i)^2+(y_k-y_i)^2+(z_k-z_i)^2}$, where $P_k=(x_k, y_k, z_k)$ are the position indicating element coordinates at the $k^{th}$ sample and $P_i=(x_i, y_i, z_i)$ are the sensor coordinates of the $i^{th}$ sample. In general, the criteria for selecting i and k may be as follows:

1 set S=0 set sample=0 NEXT_$i$: set $i=P$ (sample)
NEXT_$k$: set sample=sample+1 set $k=P$
(sample) set time=sample+1 if $\sqrt{(x_k-x_i)^2+(y_k-y_i)^2+(z_k-z_i)^2}$>threshold distance $S=S+\sqrt{(x_k-x_i)^2+(y_k-y_i)^2+(z_k-z_i)^2}$//distance from sample 0 to sample $k$.//calculate corresponding point in image space, of distance $S$ from the start set sample=sample+1 if more samples: go to NEXT_$i$ else if more samples: go to NEXT_$k$ Once position indicating element 715 moves more than a predefined amount (the threshold distance), S can be calculated from the image data showing the path of registration device 713. Unless this is done, noise will be continually added to the estimate of S, and the estimates of S will always be higher than the correct measurements. At corresponding values of S, the data from the image data (image space) is matched to the position indicating element space data (patient space), producing a high quality paired point matching at locations all along catheter 701.

Having determined an image space set of coordinates of the path of catheter 701 and a patient space set of coordinates of the same path, registration may be performed between the position data of the patient space and the imaging data of the patient space. As discussed, this registration may involve calculation of a transformation matrix to bring the two sets of data from different coordinate systems into coincidence with one another. In one embodiment, additional coordinate sets may also be "co-registered" with the image and tracking coordinates. In a non-rigid registration, the registration matrix may be allowed to vary over time and location in the registered region.

Once an anatomical region has been registered, a tube, a navigation device, therapeutic tools, needles, probes, flexible endoscopes, stents, coils, drills, ultrasound transducers, pressure sensors, or indeed any flexible or rigid device that is equipped with a position indicating element may be inserted into the respective conduit and used for navigation purposes, for a therapeutic or other medical procedure, or for other purposes. In one embodiment, the registration may be used to generate or highlight an image wherein the navigable conduit is visible. The position indicating element of the device or tool may be tracked by a tracking device, and the position of the device or tool may be displayed in the generated or highlighted image, enabling navigation. Additionally, verification of the registered area according to the methods described herein (or other methods) may also be performed.

In some embodiments (e.g., where contrast agent was injected into regions distal to the tip of a catheter or tube used for registration), regions distal to the tip of the catheter may be displayed in an image and navigated as well.

By way of example, in a cardiac case, it may be possible to navigate the 3D models of any structures or vessels that were enhanced distal to catheter 701. Once registration, dynamic referencing and verification have been performed (as deemed necessary), these 3D models may be used as a map (a "roadmap") to provide an indication of the current position of a position indicating element in an instrument without the need for additional fluoroscopy. Once the instrument or guidewire containing position indicating elements has achieved its target position, its location may be confirmed (if desired) using x-rays, ultrasound, or other method. Tracking may be discontinued and catheter 701 (and other elements used for navigation, registration, dynamic referencing, and verification) may be removed by sliding it over the proximal portion of the instrument or guidewire while leaving the instrument or guidewire in position. A second catheter, which may be a special-purpose catheter such as, for example, one designed for stent employment or for other purposes, may then by slid over the instrument or guidewire to perform some any number of specialized tasks or therapies at this, the target location.

In complex situations, it may be necessary to repeat some or all of the steps above to obtain revised registrations or navigable paths.

In some embodiments, the devices described herein such as, for example, a conduit (e.g., catheter), the registration device, the verification device, and/or the referencing device may be combined with one another and/or with one or more of a pressure sensor capable of monitoring fluid or gas pressure, an electrocardiograph (ECG) to monitor the phase of the heart beat, a respiratory apparatus to measure the phase of respiration, electrical sensors to measure the electrical activity in a region, or other devices. The addition of one or more of the aforementioned devices may enable position sampling to be gated to particular phases in cardiac, respiratory, or other physiological cycle. Gating involves sampling only at a particular instant during a motion. By restricting measurements to only those times when it is known that the system is in a stable or more predictable state, it may be possible to increase the accuracy of position measurements or render them more applicable to particular phases during these or other physiological cycles. Additionally, the addition of one or more of the aforementioned devices may enable measurement of the ambient blood, fluid, or air pressure and/or measurement of chemical, biological agent, or drug concentration at particular locations and possibly correlated to the phase of a given physiological cycle.

Figure 8:
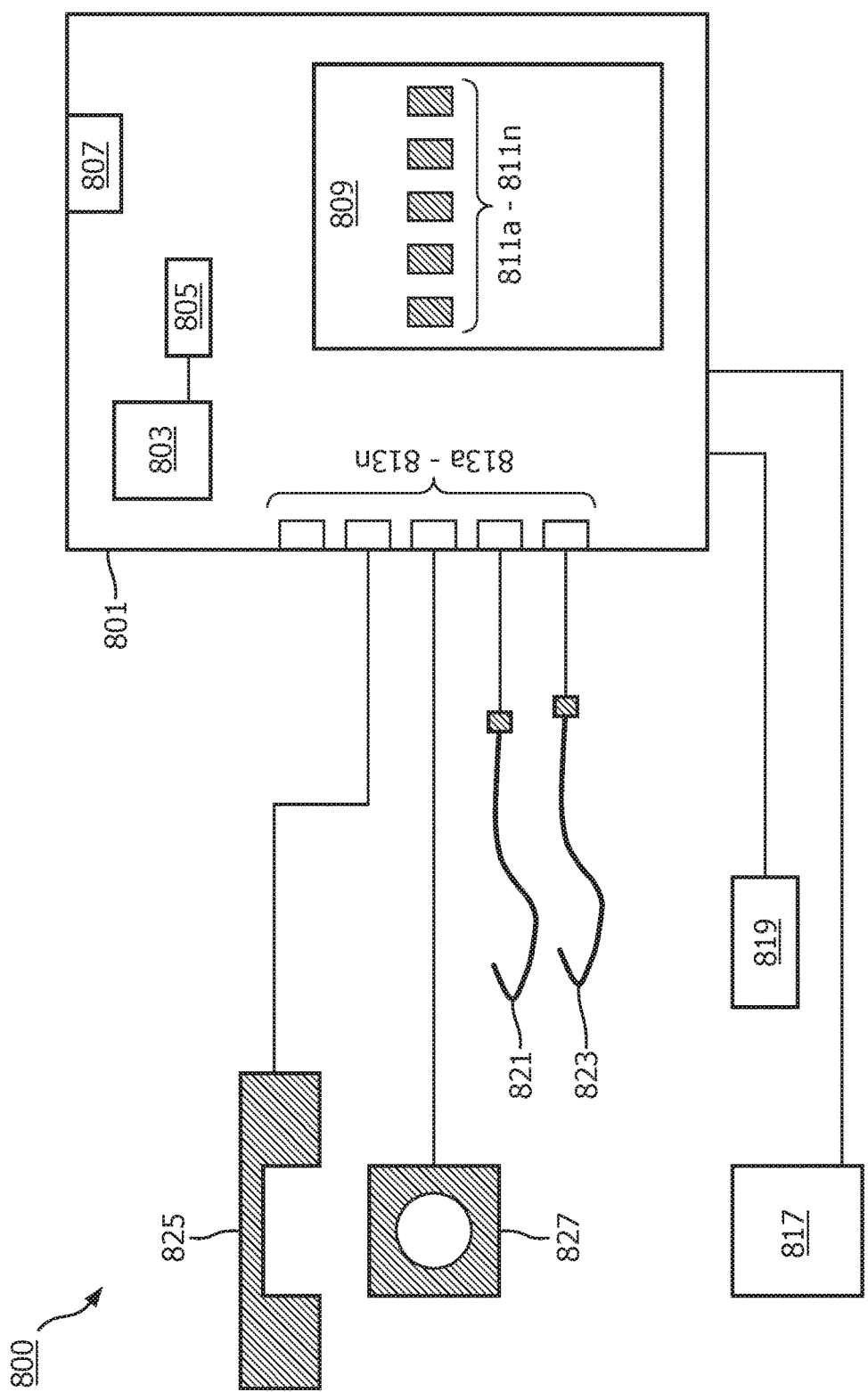
FIG. 8 is an exemplary integrated system according to an embodiment of the invention.

In some embodiments, the invention may include a computer-implemented integrated system ("integrated system") for performing one or more of the methods described herein, including any of the features, function, or operations described in FIG. 2, 3, or 5 (as well as other methods such as, for example, therapeutic, diagnostic, or other methods). The integrated system may also enable any of the devices, elements, or apparatus described herein (as well as other apparatus). FIG. 8 is an exemplary illustration of an integrated system 800 according to an embodiment of the invention. In one embodiment, an integrated system according to the invention may include a computer element 801. Computer element 801 may include a processor 803, a memory device 805, a power source 807, a control application 809, one or more software modules 811*a*-811*n*, one or more inputs/outputs 813*a*-813*n,* a display device 817, a user input device 819, and/or other elements.

Computer element 801 may include one or more servers, personal computers, laptop computers, or other computer devices. Computer element 801 may receive, send, store, and/or manipulate any data necessary to perform any of the processes, calculations, or operations described herein (including any of the features, functions, or operations described in FIG. 2, 3, or 5. Computer element 801 may also perform any processes, calculations, or operations necessary for the function of the devices, elements, or apparatus described herein.

According one embodiment, computer element 801 may host a control application 809. Control application 809 may comprise a computer application which may enable one or more software modules 811*a*-811*n*

In some embodiments, computer element 801 may contain one or more software modules 811*a*-811*n* enabling processor 803 to receive, send, and/or manipulate imaging data regarding the location, position, and/or coordinates of one or more instruments, devices, detectable elements, position indicating elements, or other elements of the invention inside an anatomical region of a patient. This imaging data may be stored in memory device 805 or other data storage location.

In some embodiments, one or more software modules 811*a*-811*n* may also enable processor 803 to receive, send and/or manipulate data regarding the location, position, orientation, and/or coordinates of one or more position indicating elements or other elements of the invention inside the anatomical region of the patient. This data may be stored in memory device 805 or other data storage location.

In some embodiments, one or more software modules 811*a*-811*n* may also enable processor 803 to calculate one or more registration transformations, perform registration (or mapping) of coordinates from two or more coordinate systems according to the one or more transformation calculations, and produce one or more images from registered data. In some embodiments, images produced from image data, position data, registration data, other data, or any combination thereof may be displayed on display device 817.

In some embodiments, one or more software modules 811*a*-811*n* may also enable processor 803 to receive, send, and/or manipulate data regarding the location, orientation, position, and/or coordinates of one or more position indicating elements for use in constructing a rigid-body description of an anatomical region of a patient. In some embodiments, one or more software modules 811*a*-811*n* may enable processor 803 to create of dynamic, deformable, and/or other models of an anatomical region of the patient, and may enable the display of real time images regarding the anatomical region. In some embodiments, these images may be displayed on display device 817.

In one embodiment, integrated system 800 may include a registration device 821 (the same as or similar to registration device 101 of FIG. 1). In some embodiments, registration device 821 may be operatively connected to computer element 801 via an input/output 813. In other embodiments, registration device 821 need not be operatively connected to computer element 801, but data may be sent and received between registration device 821 and computer element 813. Registration device 821 may, inter alia, aid in providing image data, location data, position data, and/or coordinate data regarding an anatomical region of the patient or one or more elements of the invention within the anatomical region of the patient. The registration device may otherwise enable registration of the anatomical region the patient, (including soft tissues and/or deformable bodies).

In one embodiment, integrated system 800 may include a referencing device 823 (the same as or similar to referencing device 401 of FIG. 4). In some embodiments, referencing device 823 may be operatively connected to computer element 801 via an input/output 813. In other embodiments, referencing device 823 need not be connected to computer element 801, but data may be sent and received between referencing device 823 and computer element 813. Referencing device 823 may, inter alia, aid in providing image data, location data, position data, coordinate data, and/or motion data regarding an anatomical region of the patient or one or more elements of the invention within the anatomical region of the patient. Referencing device 823 otherwise enable dynamic referencing of an anatomical region of a patient, (including soft tissues and/or deformable bodies).

In one embodiment, integrated system 800 may include a tracking device 825. In one embodiment, tracking device 825 may be operatively connected to computer element 825 via an input/output 813. In other embodiments, tracking device 825 need not be operatively connected to computer element 825, but data may be sent and received between tracking device 825 and computer element 813. Tracking device 825 may include an electromagnetic tracking device, global positioning system (GPS) enabled tracking device, an ultrasonic tracking device, a fiber-optic tracking device, an optical tracking device, a radar tracking device, or other type of tracking device. Tracking device 825 may be used to obtain data regarding the three-dimensional location, position, coordinates, and/or other information regarding one or more position indicating elements within an anatomical region of the patient. Tracking device 825 may provide this data/information to computer element 801.

In one embodiment, integrated system 800 may include an imaging device 827. In one embodiment, data may be sent and received between imaging device 827 and computer element 813. This data may be sent and received via an operative connection, a network connection, a wireless connection, through one or more floppy discs, or through other data transfer methods. Imaging device 827 may be used to obtain image data, position data, or other data necessary for enabling the apparatus and processes described herein. Imaging device 827 may provide this data to computer element 813. Imaging device 827 may include x-ray equipment, computerized tomography (CT) equipment, positron emission tomography (PET) equipment, magnetic resonance imaging (MRI) equipment, fluoroscopy equipment, ultrasound equipment, an isocentric fluoroscopic device, a rotational fluoroscopic reconstruction system, a multislice computerized tomography device, an intravascular ultrasound imager, a single photon emission computer tomographer, a magnetic resonance imaging device, or other imaging/scanning equipment Other devices and or elements such as, for example, temperature sensors, pressure sensors, motion sensors, electrical sensors, EMG equipment, ECG equipment, or other equipment or sensors may be included in and/or may send and receive data from integrated system 800. Additionally, any therapeutic diagnostic, or other medical tools or devices may also be included in and/or may send and receive data from integrated system 800.

In one embodiment, the various instruments and/or devices described herein may be interchangeably "plugged into" one or more inputs/outputs 813a-813n. In some embodiments, the software, hardware, and/or firmware included integrated system 800 may enable various imaging, referencing, registration, navigation, diagnostic, therapeutic, or other instruments to be used interchangeably with integrated system 800.

Those having skill in the art will appreciate that the invention described herein may work with various system configurations. Accordingly, more or less of the aforementioned system components may be used and/or combined in various embodiments. It should also be understood that various software modules 811a-811n and control application 809 that are used to accomplish the functionalities described herein may be maintained on one or more of the components of system recited herein, as necessary, including those within individual medical tools or devices. In other embodiments, as would be appreciated, the functionalities described herein may be implemented in various combinations of hardware and/or firmware, in addition to, or instead of, software.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

I claim:

1. A system for registering an anatomical region of a patient, comprising:
   an imaging device configured to produce image data of the anatomical region of the patient including image data coordinate information within the anatomical region in a first frame of reference;
   a registration device including at least one position indicating element;
   a restraining device comprising one of: a balloon, vacuum ports disposed along a length of the restraining device, deployable hooks, cages, or stiffening wires, the restraining device being configured to receive the registration device and to maintain the registration device slidably along a path defined by the restraining device and lying within the anatomical region set out in the image data coordinate information;
   a tracking device adapted to produce position data regarding the path defined by the restraining device as a followed path of the registration device within the anatomical region in a second frame of reference, wherein the position data is obtained by the tracking device sampling coordinates of the at least one position indicating element as the position indicating element is moved within the followed path of the registration device within the anatomical region; and
   a computer element comprising a processor, wherein the processor is adapted to receive the image data including an image data path of the registration device in the image data coordinate information from the imaging device, receive the position data including the followed path of the registration device in the position data from the tracking device, and map the image data path of the registration device from the image data coordinate information and the followed path of the registration device from the position data together.

2. The system of claim 1, wherein the imaging device includes one of an x-ray device, an ultrasound device, a fluoroscopic device, a computerized tomography device, a positron emission tomography device, an isocentric fluoroscope, a rotational fluoroscopic reconstruction system, a multislice computerized tomography device, an intravascular ultrasound imager, a single photon emission computer tomographer, or a magnetic resonance imaging device.

3. The system of claim 1, wherein the registration device comprises a lumen disposed into the anatomical region, and one or more points on the image data path of the registration device from the image data coordinate information of the anatomical region corresponds to position data of the lumen.

4. The system of claim 3, wherein the lumen comprises one of a tube, a catheter, or a lumen within a flexible endoscope.

5. The system of claim 1, wherein the registration device comprises a first manufactured device comprising a first lumen disposed within a second manufactured device comprising a second lumen disposed within a naturally existing vessel.

6. The system of claim 1, wherein the registration device includes at least one lumen, wherein the registration device has first and second ends, and wherein at least one of the first or second ends is closed.

7. The system of claim 1, wherein the tracking device comprises one of an ultrasonic tracking device, a fiber-optic tracking device, a global positioning system enabled tracking device, an optical tracking device or a radar tracking device.

8. The system of claim 1, wherein the at least one position indicating element comprises a wire coil that produces a magnetic field, and wherein the tracking device comprises an electromagnetic tracking device that detects the magnetic field.

9. The system of claim 1, wherein the at least one position indicating element comprises a wire coil that detects a magnetic field, and wherein the tracking device comprises an electromagnetic tracking device that produces the magnetic field.

10. A computer-implemented method for registering an anatomical region of a patient, comprising:
receiving image data of the anatomical region in a first frame of reference from an imaging device, the image data including image data of an image data path within the anatomical region;
receiving position data from a registration device slidably disposed in a restraining device comprising one of: a balloon, vacuum ports disposed along a length of the restraining device, deployable hooks, cages, or stiffening wires, the restraining device being configured to maintain the registration device along a path defined by the restraining device as a followed path within the anatomical region, wherein the position data is in a second frame of reference, the second frame of reference being of a tracking device, wherein the position data is obtained by the tracking device sampling a position of at least one position indicating element as the position of the at least one position indicating element moves following the followed path; and
mapping the image data path of the image data and the followed path of the position data together using a registration transformation.

11. The computer-implemented method of claim 10, wherein the imaging device includes one of an x-ray device, an ultrasound device, a fluoroscopic device, a computerized tomography device, a positron emission tomography device, an isocentric fluoroscope, a rotational fluoroscopic reconstruction system, a multi-slice computerized tomography device, an intravascular ultrasound imager, a single photon emission computer tomographer, or a magnetic resonance imaging device.

12. The computer-implemented method of claim 10, wherein the registration device comprises a lumen that has been inserted into the anatomical region, and wherein the lumen comprises one of a tube, a catheter, or a lumen within a flexible endoscope.

13. The computer-implemented method of claim 10, wherein the image data path within the image data coordinate information of the anatomical region includes a manufactured device comprising a lumen within a naturally existing vessel.

14. The computer-implemented method of claim 10, wherein the image data path within the image data coordinate information within the anatomical region includes a first manufactured device comprising a lumen within a second manufactured device comprising a lumen within a naturally existing vessel.

15. The computer-implemented method of claim 10, wherein the tracking device comprises one of an ultrasonic tracking device, a fiber-optic tracking device, a global positioning system enabled tracking device, an optical tracking device or a radar tracking device.

16. The computer-implemented method of claim 10, wherein the position of the at least one position indicating element comprises a wire coil that produces a magnetic field, and wherein the tracking device comprises an electromagnetic tracking device that detects the magnetic field.

17. The computer-implemented method of claim 10, wherein the position of the at least one position indicating element comprises a wire coil that detects a magnetic field, and wherein the tracking device comprises an electromagnetic tracking device that emits the magnetic field.

18. A method for registering an anatomical region of a patient, the method comprising:
imaging the anatomical region using an imaging device to produce image data of the anatomical region including image data coordinate information of an imaging data path in a first frame of reference;
slidably disposing a registration device in a restraining device, wherein the restraining device comprises one of: a balloon, vacuum ports disposed along a length of the restraining device, deployable hooks, cages, or stiffening wires;
inserting the registration device having first and second ends into a path within the anatomical region, wherein the first end of the registration device is inserted into the path within the anatomical region, and wherein the registration device includes at least one position indicating element located at the first end of the registration device;
moving the registration device within the restraining device along the path within the anatomical region while sampling coordinates of the at least one position element to produce position data regarding a path of the registration device defined by the restraining device as a path of the registration device within the anatomical region in a second frame of reference, wherein coordinates of the one or more position indicating elements are sampled by a tracking device; and
mapping together the imaging data path of the image data and the followed path of the position data using a registration transformation to produce a set of registration data for the followed path of the registration device relative to the imaging data path within the image data of the anatomical region.

19. The method of claim 18, wherein the imaging device includes one of an x-ray device, an ultrasound device, a fluoroscopic device, a computerized tomography device, a positron emission tomography device, an isocentric fluoroscope, a rotational fluoroscopic reconstruction system, a multi-slice computerized tomography device, an intravascular ultrasound imager, a single photon emission computer tomographer, or a magnetic resonance imaging device.

20. The method of claim 18, wherein imaging the anatomical region further comprises inserting the registration device into the anatomical region so that the followed path of the registration device at least partially fills a space within the anatomical region.

21. The method of claim 18, wherein inserting a registration device further comprises inserting the registration device through an orifice within the patient.

22. The method of claim 18, wherein inserting a registration device further comprises inserting the registration device through an orifice within the patient, and wherein the orifice is a naturally occurring orifice.

23. The method of claim 18, wherein inserting a registration device further comprises inserting the registration device through an orifice within the patient, and wherein the orifice is created during a surgical procedure.

24. The method of claim 18, wherein the image data path within the image data coordinate information the anatomical region includes a naturally existing vessel, and wherein the naturally existing vessel comprises one of a circulatory vessel, a respiratory vessel, a lymphatic vessel, a urinary tract vessel, a cerebrospinal fluid vessel, a reproductive vessel, an auditory vessel, or a digestive vessel.

25. The method of claim 18, wherein the registration device comprises a manufactured device comprising a lumen that has been inserted into the anatomical region, and wherein the restraining device comprises one of a tube, a catheter, or a lumen of a flexible endoscope.

26. The method of claim 18, wherein the image data path within the image data coordinate information of the anatomical region comprises a manufactured device comprising a lumen within a naturally existing channel.

27. The method of claim 18, wherein the registration device comprises a first manufactured device comprising a lumen within a second manufactured device comprising a lumen within a naturally existing vessel.

28. The method of claim 18, wherein the tracking device comprises one of an ultrasonic tracking device, a fiber-optic tracking device, a global positioning system enabled tracking device, an optical tracking device or a radar tracking device.

29. The method of claim 18, wherein the at least one position indicating element comprises a wire coil that produces a magnetic field, and wherein the tracking device comprises an electromagnetic tracking device that detects the magnetic field.

30. The method of claim 18, wherein the at least one position indicating element comprises a wire coil that detects a magnetic field, and wherein the tracking device comprises an electromagnetic tracking device that emits the magnetic field.

31. The method of claim 18, further comprising: displaying a location of the registration device within the image data path within the image data coordinate information of the anatomical region on an image of the anatomical region; inserting a verification device having one or more verification position indicating elements into the image data path within the image data coordinate information; calculating a location of the one or more verification position indicating elements on the image of the anatomical region using the registration transformation; and comparing the location of the one or more verification position indicating elements to the location of the registration device.

32. The method of claim 18, further comprising: inserting one or more referencing position indicating elements into the image data path within the image data coordinate information; obtaining spatial relationship data regarding the one or more referencing position indicating elements relative to one another; creating a model of the anatomical region using the spatial relationship data; sampling movement of the one or more referencing position indicating elements; and applying the sampled movement to the model of the anatomical region to create a dynamic model of the anatomical region.

* * * * *